(12) United States Patent  (10) Patent No.: US 8,519,613 B2
Kamatani et al.  (45) Date of Patent: Aug. 27, 2013

(54) ORGANIC LIGHT-EMITTING DEVICE

(75) Inventors: Jun Kamatani, Tokyo (JP); Isao Kawata, Kawasaki (JP); Naoki Yamada, Inagi (JP); Akihito Saitoh, Yokohama (JP); Hiroyuki Tomono, Tokyo (JP); Kengo Kishino, Tokyo (JP); Masashi Hashimoto, Tokyo (JP); Satoshi Igawa, Fujisawa (JP); Keiji Okinaka, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 69 days.

(21) Appl. No.: 13/330,334

(22) Filed: Dec. 19, 2011

(65) Prior Publication Data

US 2012/0085996 A1 Apr. 12, 2012

Related U.S. Application Data

(63) Continuation of application No. 12/639,847, filed on Dec. 16, 2009, now Pat. No. 8,102,116.

(30) Foreign Application Priority Data

Dec. 19, 2008 (JP) ................................. 2008-324470

(51) Int. Cl.
H01L 51/50 (2006.01)
H01L 51/52 (2006.01)

(52) U.S. Cl.
USPC ............ 313/504; 313/501; 313/503; 428/690

(58) Field of Classification Search
USPC ................... 313/500–512; 428/690
See application file for complete search history.

(56) References Cited

U.S. PATENT DOCUMENTS

| | | | |
|---|---|---|---|
| 6,242,858 B1 * | 6/2001 | Sun ............................... | 313/503 |
| 2005/0249972 A1 | 11/2005 | Hatwar | |
| 2010/0157133 A1 * | 6/2010 | Kosaka et al. ................. | 348/340 |

FOREIGN PATENT DOCUMENTS

JP 2001167890 A * 6/2001

OTHER PUBLICATIONS

Jie Liu, et al., "Improving the performance of polymer light-emitting diodes using polymer solid solutions", Applied Physics Letters, vol. 79, No. 5, Jul. 30, 2001, pp. 578-590.

* cited by examiner

*Primary Examiner* — Mariceli Santiago
(74) *Attorney, Agent, or Firm* — Canon U.S.A., Inc., IP Division

(57) ABSTRACT

An organic light-emitting device includes a first electrode, a second electrode, and a light-emitting layer disposed between the first and second electrodes. The light-emitting layer contains an organic compound emitting photoluminescent light with a peak wavelength of 430 to 480 nm. The organic compound has a profile factor of 0.02 or less at a wave number of 1,300 to 1,680 cm$^{-1}$ as calculated from Huang-Rhys factors.

32 Claims, 27 Drawing Sheets a : SHORT-WAVELENGTH REGION OF
    FULL WIDTH AT HALF MAXIMUM
b : LONG-WAVELENGTH REGION OF
    FULL WIDTH AT HALF MAXIMUM

FIG. 7
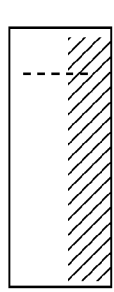 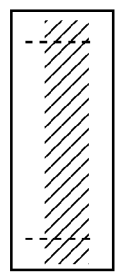 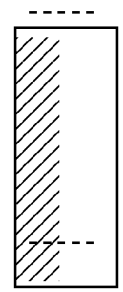
EXAMPLE 4   EXAMPLE 5   EXAMPLE 6

ORGANIC LIGHT-EMITTING DEVICE

CROSS REFERENCE TO RELATED APPLICATIONS

This application is a Continuation of U.S. patent application Ser. No. 12/639,847 filed Dec. 16, 2009, which claims priority to Japanese Patent Application No. 2008-324470 filed Dec. 19, 2008, each of which are hereby incorporated by reference herein in their entireties.

BACKGROUND OF THE INVENTION

1. Field of the Invention

The present invention relates to an organic light-emitting device and an image display apparatus including pixels including organic light-emitting devices.

2. Description of the Related Art

Organic light-emitting devices each include an anode, a cathode, and a thin-film which contains a fluorescent organic compound and which is sandwiched between the anode and the cathode. Electrons and holes are injected into the thin-film from the cathode and the anode, respectively, whereby excitons are produced in the fluorescent organic compound. Light is emitted from the fluorescent organic compound when the excitons return to the ground state.

The organic light-emitting devices are referred to as organic electroluminescent devices or simply as organic EL devices.

In recent years, the organic light-emitting devices have been remarkably improved. Therefore, the organic light-emitting devices have high brightness at low voltage and fast response, emit light with various wavelengths, and can be transformed into thin, lightweight devices. This suggests that the organic light-emitting devices have various possible applications.

In the past, organic compounds for use in light-emitting devices have been extensively investigated. This is because light-emitting properties of an organic compound and the configuration of an organic light-emitting device affect the performance of the organic light-emitting device and therefore are important.

The following documents disclose materials for use in light-emitting layers and improvements in color purity of light-emitting devices: Japanese Patent Laid-Open Nos. 2000-323279, 2002-299058, 2004-206893, and 8-213174 and WO 00/39247.

Organic light-emitting devices disclosed in the above documents need to be improved for practical use.

In particular, these organic light-emitting devices need to emit brighter light or need to have higher conversion efficiency. Furthermore, these organic light-emitting devices need to be improved in durability so as not to be deteriorated with time for long periods or so as not to be deteriorated by atmospheric gases or humidity.

Organic light-emitting devices applied to full-color displays need to emit blue light with high color purity at high efficiency. However, this issue has not yet been satisfactorily resolved.

Therefore, the following compounds, devices, and techniques need to be designed: organic compounds having high color purity, luminous efficiency, and durability; organic light-emitting devices capable of efficiently using such organic light-emitting devices; and techniques for designing molecules for achieving such purposes.

SUMMARY OF THE INVENTION

The present invention provides an organic light-emitting device including a first electrode, a second electrode, and a light-emitting layer disposed between the first and second electrodes. The light-emitting layer contains an organic compound emitting photoluminescent light with a peak wavelength of 430 to 480 nm. The organic compound has a profile factor of 0.02 or less at a wave number of 1,300 to 1,680 $cm^{-1}$ as calculated from Huang-Rhys factors.

The organic light-emitting device can efficiently emit bright light.

Further features of the present invention will become apparent from the following description of exemplary embodiments with reference to the attached drawings.

BRIEF DESCRIPTION OF THE DRAWINGS

FIG. 7 is an illustration showing the highest occupied molecular orbital, lowest unoccupied molecular orbital, and luminescent center of each of a host material and a guest material.

DESCRIPTION OF THE EMBODIMENTS

Figure 1:
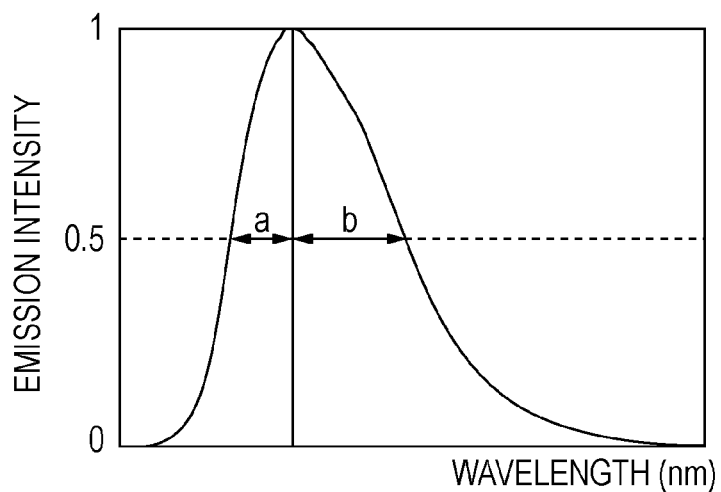
FIG. 1 is a graph illustrating the short-wavelength region and long-wavelength region of a full width at half maximum.

A first embodiment of the present invention provides an organic light-emitting device including a pair of electrodes and a light-emitting layer disposed between the electrodes. The light-emitting layer contains an organic compound emitting photoluminescent light with a peak wavelength of 430 to 480 nm. The organic compound has a profile factor of 0.02 or less at a wave number of 1,300 to 1,680 $cm^{-1}$ as calculated from Huang-Rhys factors.

The organic light-emitting device can emit blue light with high color purity.

In this embodiment, the factor electrode and the second electrode are a cathode and anode, respectively, for supplying electrons and holes, respectively; to the light-emitting layer.

The organic light-emitting device has a reflective surface reflecting the light emitted from the light-emitting layer and a light-extracting surface through which the light emitted from the light-emitting layer is extracted.

The optical path from the light-emitting layer to the reflective surface is set such that light is amplified. The expression "light is amplified" as used herein means that a first portion and second portion of the light emitted from the light-emitting layer stimulate each other, the first portion traveling outside without being reflected, the second portion being reflected by the reflective surface and then traveling outside.

A member carrying the reflective surface is disposed in contact with one of the electrodes.

The reflective surface is not located between the electrodes. The other one of the electrodes is located on the light-extracting surface side of the organic light-emitting device. The light emitted from the light-emitting layer is reflected by the reflective surface and is then extracted through the light-extracting surface.

The optical path from the light-emitting layer to the reflective surface is given by the following equation:

$$L=(2N-1)\lambda/4+\Phi$$

wherein L is the optical path from the light-emitting layer to the reflective surface, $\lambda$ is the peak wavelength (in nm) of the light emitted from the light-emitting layer, N is a positive integer, and $\Phi$ is a phase shift.

That is, the organic light-emitting device includes an anode, a cathode, and alight-emitting layer disposed between the anode and the cathode. The light emitted from the light-emitting layer is reflected by the reflective surface and is then extracted through the light-extracting surface. The light-emitting layer contains an organic compound emitting photoluminescent light with a peak wavelength of 430 to 480 nm. The organic compound has a profile factor of 0.02 or less at a wave number of 1,300 to 1,680 $cm^{-1}$ as calculated from Huang-Rhys factors. The optical path from the light-emitting layer to the reflective surface is given by the following equation:

$$L=(2N-1)\lambda/4+\Phi$$

wherein L is the optical path from the light-emitting layer to the reflective surface, $\lambda$ is the peak wavelength (in nm) of the light emitted from the light-emitting layer, N is a positive integer, and $\Phi$ is a phase shift.

The organic light-emitting device is further described below in detail.

The inventors have thought that in order to provide an organic light-emitting device capable of emitting bright light with high efficiency, an organic compound needs to be optimally designed.

In general, keys to increasing the emission efficiency of organic light-emitting devices are the enhancement of properties of materials used and the optimization of the configuration of the organic light-emitting devices.

For such purposes, at least one of items below needs to be accomplished.

1. To achieve a luminescent material with high quantum yield.
2. To achieve a luminescent material with a narrow half-width.
3. To efficiently extract light from a luminescent material.

Luminescent materials for use in a full-color organic EL display need to each emit blue, green, or red light. The full-color organic EL display is an image display apparatus capable of displaying a full-color image. The image display apparatus includes a plurality of pixel. The pixels each include a plurality of sub-pixels having different colors so as to provide full-color emission. Each of the sub-pixels includes an organic light-emitting device. Alternatively, the pixels each include, for example, different sub-pixels emitting red, green, or blue light.

Blue light has a peak wavelength of 430 to 480 nm, green light has a peak wavelength of 490 to 540 nm, and red light has a peak wavelength of 590 to 640 nm.

In order to accomplish Item 1, it is important to increase the symmetry of a molecular framework involved in light emission. Some of highly symmetric molecules emit no light under forbidden transition conditions characteristic thereof. The elongation of conjugation sequences in the same direction increases the moment of a molecule to enhance the oscillator strength.

The lack of a rotational structure in such a molecular framework involved in light emission allows the reduction in quantum yield due to rotational vibration to be prevented.

Therefore, in order to produce an organic compound with high quantum yield, it is important to prevent the organic compound from having a rotational structure in a framework having an electron distribution involved in light emission.

In order to accomplish Item 2, the following two techniques are available: a technique for producing an organic compound with a novel molecular structure and a technique for improving the configuration of an organic light-emitting device.

Light-emitting devices for use in pixels in full-color organic EL displays need to have an emission spectrum with high color purity.

In order to obtain high color purity, the following organic compound probably needs to be developed: an organic compound that has a maximum emission peak with a narrow full width at half maximum and also has a vibration peak with a small height in an emission spectrum obtained from a solution containing this compound. The term "maximum emission peak" as used herein means an emission peak having the highest intensity.

In order to emit light having an emission peak with a narrow full width at half maximum and high color purity, an organic compound having a maximum emission peak with a narrow full width at half maximum needs to be developed.

The carbon-carbon vibration affects the spectrum of the light emitted from an organic compound. Therefore, a long-wavelength region b of a full width at half maximum is greater than a short-wavelength region a thereof as shown in FIG. 1. The inventors have found that this is a cause of increasing the full width at half maximum. In an organic compound, the increase of long-wavelength region b of the full width at half maximum is allowable to a certain extent. The inventors think that this causes a reduction in color purity.

All wavelengths other than a target wavelength cause a reduction in color purity.

A reduction in color purity can occur in any chromaticity region.

The inventors have found the following.

Figure 2:
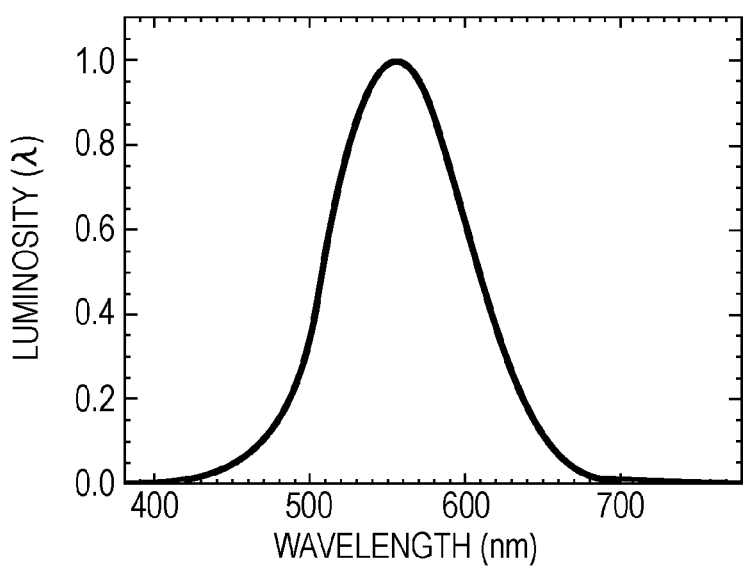
FIG. 2 is a graph illustrating a luminosity curve.

The blue light range and the 420-500 nm wavelength range are important in view of luminosity. FIG. 2 is a graph illustrating a luminosity curve. Luminosity sharply increases with an increase in wavelength as shown in FIG. 2. When an organic blue light-emitting device emits light with long wavelengths, the light emitted therefrom contains a color component which is not desired and which is conspicuous. Therefore, even light with a peak wavelength of 440 to 480 nm can affect chromaticity.

That is, the blue light range has low luminosity and further has low chromaticity due to the long-wavelength region b of the full width at half maximum.

Figure 3:
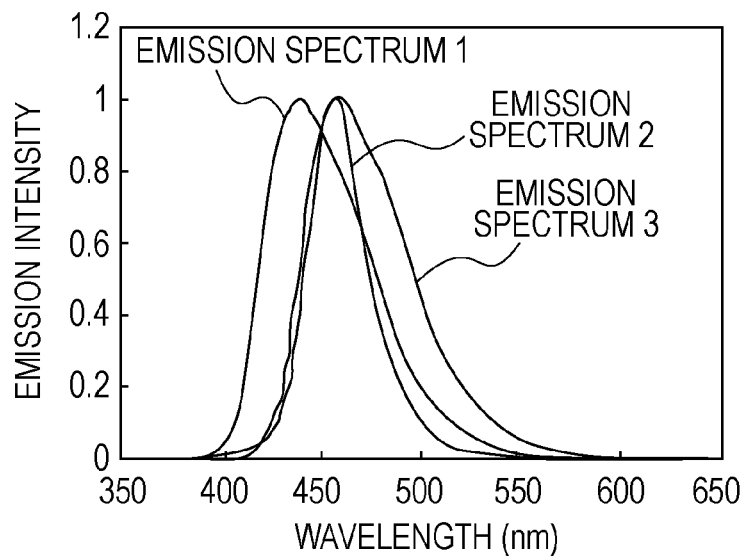
FIG. 3 is a graph illustrating Emission Spectra 1 to 3.

FIG. 3 illustrates Emission Spectra 1 to 3. With reference to FIG. 3, Emission Spectrum 1 has a broad peak at short wavelengths, Emission Spectrum 2 has a peak with a narrow full width at half maximum, and Emission Spectrum 3 has a broad peak at long wavelengths.

Table 1 summarizes the X and Y chromaticity coordinates corresponding to Emission Spectra 1 to 3.

TABLE 1

| Emission Spectra | Chromaticity | |
|---|---|---|
| | X | Y |
| 1 | 0.14 | 0.06 |
| 2 | 0.14 | 0.05 |
| 3 | 0.13 | 0.12 |

Emission Spectrum 1, which has a broad peak at short wavelengths, is not significantly different in chromaticity from Emission Spectrum 2, which has a peak with a narrow full width at half maximum. This is because the 400-420 nm wavelength range has extremely low luminosity and therefore light in the 400-420 nm wavelength range is hardly visible.

Emission Spectra 2 and 3 both have a peak wavelength of about 460 nm. The Y chromaticity coordinate of Emission Spectrum 3, which has a broad peak at long wavelengths, is considerably greater than that of Emission Spectra 2. This is because Emission Spectra 2 and 3 have overlapping portions in the 450-460 nm wavelength range and only Emission Spectrum 3 has a portion in the 490-500 nm wavelength range, which has luminosity two to three times greater than that of the 450-460 nm wavelength range. This causes such a large difference in chromaticity.

Light with a wavelength of 420 nm or less is in the blue light range and is, however, not recognized as blue visible light. Therefore, light with a wavelength of 420 nm or less is not significantly different in chromaticity from light with a wavelength of more than 420 nm and, however, has a useless portion.

On the other hand, light with a wavelength of 490 nm or more causes a reduction in color purity and therefore is inappropriate for organic light-emitting devices emitting blue light with high color purity.

Therefore, in order to achieve organic light-emitting devices emitting blue light with high color purity, the full width at half maximum of the emission spectrum of a material used needs to be reduced.

Light with high color purity can be achieved by improving the configuration of a light-emitting device. For example, a technique using an optical resonator structure can be used. One or more layers each carrying a reflective surface are provided on one or both surface sides of the light-emitting layer, whereby an optical microresonator is configured. Light resonated in the optical microresonator is amplified and can be emitted so as to have a wavelength corresponding to the resonant frequency thereof. The reflective surface-carrying layer may be, for example, one of electrodes included in an organic light-emitting device.

The organic light-emitting device has a light-extracting surface through which the light emitted from the light-emitting layer is extracted.

The organic light-emitting device further has a reflective surface placed separately from the light-extracting surface. In particular, the reflective surface is located opposite the light-extracting surface.

For example, a layer carrying a semitransparent reflective surface is formed on a substrate. A transparent conductive layer is formed on the semitransparent reflective surface-carrying layer. At least one hole injection layer, a light-emitting layer including an organic thin-film, at least one electron injection layer, and an electrode are formed on the transparent conductive layer in that order. A portion of the light emitted from the light-emitting layer passes through the semitransparent reflective surface-carrying layer to travel toward a transparent base. The electrode, which is disposed on the electron injection layer, reflects another portion of the light emitted therefrom. Therefore, the semitransparent reflective surface-carrying layer and the electrode, which is disposed on the back of the light-emitting layer (or which is disposed on the electron injection layer), form an optical resonator. The transparent conductive layer, which is located close to the substrate, serves as an anode and the electrode, which is located far away from the substrate and is disposed on the electron injection layer, serves as a cathode. The light emitted from the light-emitting layer passes through the semitransparent reflective surface, which is located close to a light-extracting surface, and the substrate to travel outside. These layers need to be designed such that the following equation holds:

$$L=(2N-1)\lambda/4+\Phi$$

wherein L is the optical path, $\lambda$ is the peak wavelength (in nm) of the light emitted from the light-emitting layer, N is a positive integer, and $\Phi$ is a phase shift. In particular, the thickness of each of these layers is appropriately determined.

The thickness of each of these layers is preferably precisely determined on a nanometer level. In consideration of an allowance, the thickness thereof is preferably determined within ±10 nm of a thickness satisfying the above equation and more preferably ±5 nm. This allows a resonator structure to be well formed.

The optical path L of the resonator structure is equal to the sum of the optical paths of layers present between the interface between the semitransparent reflective surface-carrying layer and the transparent conductive layer and the interface between the electron injection layer and a semitransparent layer and is given by the formula ($n_1 d_1 + n_2 d_2 + n_3 d_3 + \ldots$), wherein n is the refractive index of each layer and d is the thickness of the layer.

The phase shift $\Phi$ at a reflective interface is given by the following equation:

$$\Phi = \tan^{-1}(2n_1 k_1 / (n_1^2 - n_1^2 - k_1^2)) \qquad (1)$$

wherein $0 \leq \Phi \leq 2\pi$.

The reflective interface is between two materials: Medium I which is one of the materials that is on the light incident side of the reflective interface and Medium II which is the other one. Medium I has optical constants ($n_1$, $k_1$): $n_1$ is the refractive index and $k_1$ is the extinction coefficient. Medium II has optical constants ($n_2$, $k_2$): $n_2$ is the refractive index and $k_2$ is the extinction coefficient. These optical constants can be determined with, for example, a spectroscopic ellipsometer or the like. For a reflective interface which is disposed between a reflective layer and transparent electrode layer arranged in an organic light-emitting device, the transparent electrode layer is on the light incident side of the reflective interface and corresponds to Medium I and the reflective layer corresponds to Medium II. For a reflective interface which is disposed between an electron injection layer and a semitransparent layer, the electron injection layer corresponds to Medium I and the semitransparent layer corresponds to Medium II. The phase shift $\Phi$ is equal to the sum of the phase shifts at these interfaces.

An organic compound has a refractive index of about 1.3 to 2.1 and a multilayer film containing such an organic compound has a refractive index of about 1.6 to 1.7 depending on the configuration thereof.

When N is an integral multiple of 1, 2, 3, 4, 5, ..., or n, resonance can be caused. A reduction in N increases the effect of resonance and an increase in N reduces the effect of resonance; hence, N is preferably 1 to 4. When N is 1, the effect of resonance is highest.

Light with high color purity can be obtained by improving the configuration of a device as described above.

The improvement of the device configuration into a resonator structure is a solution to increase the color purity of the light emitted from a material by not extracting a portion with low chromaticity from the light emitted therefrom. For this improvement, the quantum yield of light emission from the resonator structure is less than the quantum yield of this material.

The inventors have found that it is insufficient to introduce an optical resonator structure into an organic light-emitting device and also have found that it is insufficient to focus the desired peak wavelength of the light emitted from a material, that is, an organic compound contained in a light-emitting layer. The inventors have thought that it is necessary to develop an organic compound with implications for luminosity and a developed organic compound is useful in increasing the quantum yield of an organic light-emitting device which has an optical resonator structure and which emits light of a desired color.

Considerations on the efficient extraction of light from such a luminescent material as described in Items 1 to 3 are described below.

In order to accomplish Item 3, it is important to make use of the luminescence or photoluminescence of a material contained in an organic light-emitting device.

Figure 4:
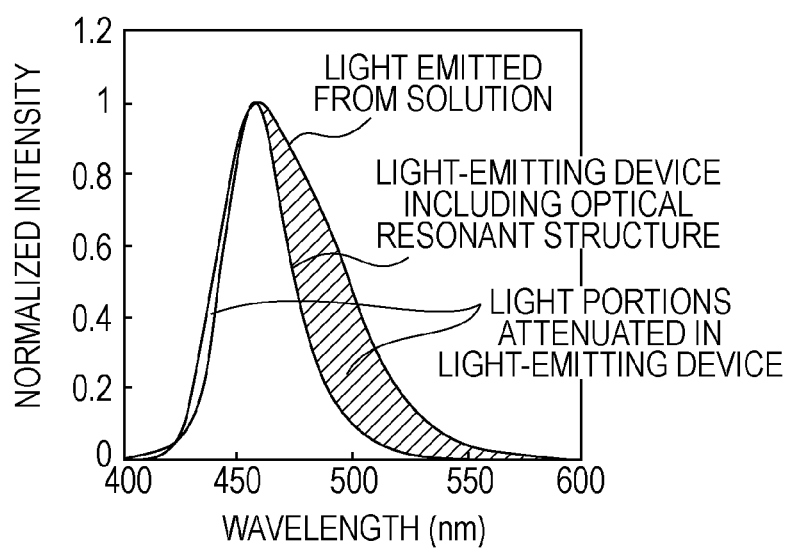
FIG. 4 is a graph illustrating the photoluminescence spectrum of an organic compound and the electroluminescence spectrum of the organic compound used in an optical resonator structure.

In order to achieve that, such a requirement for the material as described above in Item 2 and a requirement for the device configuration need to be both satisfied. FIG. 4 is a graph illustrating the emission (photoluminescence) spectrum of an organic compound in a solution and the emission (electroluminescence) spectrum of the organic compound used in an optical resonator structure. A region where these spectra do not overlap with each other is diagonally hatched.

As shown in FIG. 4, the light emitted from a device using the optical resonator structure is attenuated except a light portion with a wavelength close to a target peak wavelength. For a material emitting light with a full width at half maximum more than, for example, 30 nm, a light portion with a wavelength 30 nm longer than a peak wavelength is attenuated, which causes a reduction in the quantum efficiency of the extraction of light from the device.

Therefore, the inventor think that the requirements for both the material and the device configuration are important in developing an organic light-emitting device emitting light with high color purity without sacrificing efficiency.

Figure 5:
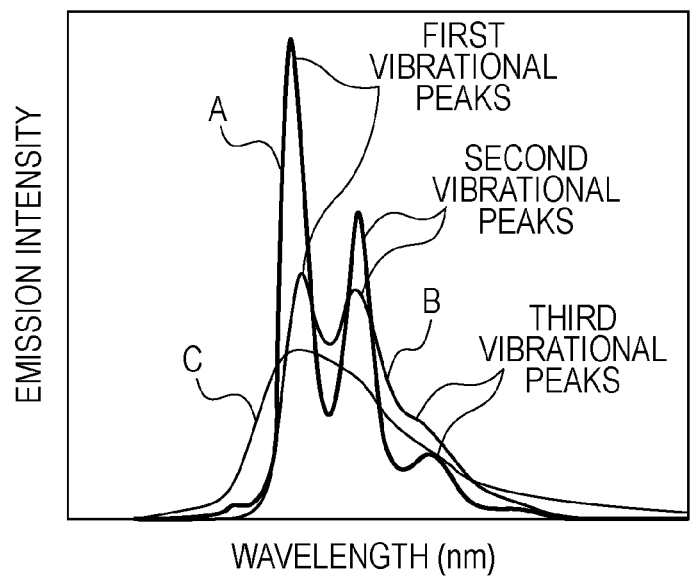
FIG. 5 is a graph illustrating Spectra A, B, and C.

A material with a narrow full width at half maximum is defined as a material having an emission spectrum with clear vibrational peaks (clearly separated from each other). FIG. 5 shows Spectra A, B, and C which have the same emission area (the same quantum yield) and different waveforms. Light with Spectrum C, which has no vibrational peaks and therefore has an unclear vibrational structure, usually has a broad emission waveform with a wide full width at half maximum. In contrast, light with Spectrum A or B, which has clear vibrational peaks, has a first vibrational peak which is the maximum and which has high intensity and a narrow full width at half maximum. Unlike Spectrum C, Spectra A and B correspond to the spectrum of the light emitted from an organic compound with a clear vibrational structure.

In comparison with Spectrum A, Spectrum B has a first vibrational peak and second vibrational peak that are not sufficiently different in intensity (emission intensity on the ordinate of FIG. 5) from each other. Even in an emission spectrum with a vibrational structure, vibrational peaks thereof are not so large in intensity. This is because since there are many molecular vibrational modes, a second vibrational peak and a vibrational peak subsequent thereto are large and a first vibrational peak is relatively small. Furthermore, this is because light portions to be attenuated cause an area difference with respect to a height ratio and therefore a difference corresponding to the square of height occurs.

When the height ratio of a first vibrational peak to a second vibrational peak is 1:0.7 (supposing that light used has high vibrational peaks), the area ratio thereof is about 2:1 by conversion. The inventors predict that an increase in the height ratio thereof increases the areas of light portions to be attenuated in a light-emitting device and therefore causes a reduction in light extraction efficiency.

Spectrum A has a clear vibrational structure and also has a first vibrational peak and a second vibrational peak and the height ratio of the second vibrational peak to the first vibrational peak is 0.7 or less; hence, emission spectra similar to Spectrum A are preferred. The height of the second vibrational peak is zero or more of that of the first vibrational peak at least. When the height ratio of the second vibrational peak to the first vibrational peak is greater than 0.7, the percentage of a light portion attenuated by the use of a resonator structure is large. This causes a reduction in quantum efficiency.

Figure 6:
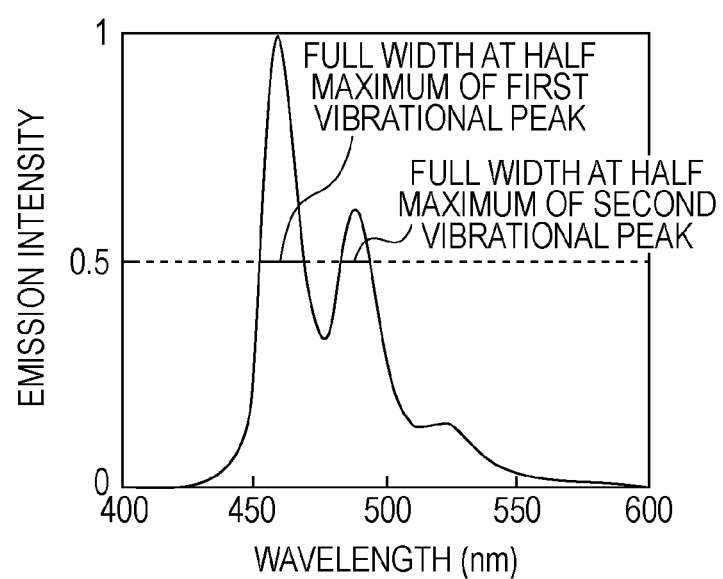
FIG. 6 is a graph illustrating the relationship between the full width at half maximum of a first vibrational peak and that of a second vibrational peak.

When a first vibrational peak has high intensity, the first vibrational peak overlaps with a second vibrational peak as shown in FIG. 6.

FIG. 6 is a graph illustrating the relationship between the full width at half maximum of the first vibrational peak and that of the second vibrational peak.

The term "full width at half maximum" usually means the full width of a peak at one-half of the intensity of the peak.

In such a waveform as shown in FIG. 6, the first and second vibrational peaks are sufficiently spaced from each other. According to the definition of an ordinary full width at half maximum, there are two full widths at half maximum in this waveform: the full width at half maximum of the first vibrational peak and the full width at half maximum of the second vibrational peak. This is confusing. Therefore, the term "full width at half maximum" as used herein means the full width at half maximum of the first vibrational peak in this waveform.

The waveform shown in FIG. 6 has a valley between the first and second vibrational peaks. The intensity of the second vibrational peak is greater than half of the intensity of the first vibrational peak.

With reference to FIG. 6, the full width at half maximum of the second vibrational peak is represented by the width of the second vibrational peak at an intensity of 0.5.

Such an emission spectrum is a feature of a luminescent material that is designed herein to have a narrow full width at half maximum. This luminescent material preferably has a first vibrational peak with a full width at half maximum of 30 nm or less.

In order to satisfy these conditions, it is important herein to design a material which has a first vibrational peak with a narrow full width at half maximum and a second vibrational peak far less than the first vibrational peak and which has high quantum yield.

The luminescent center of the light-emitting layer is described below.

The light-emitting layer contains the organic compound as described above. The organic compound emits light when receiving energy.

The light-emitting layer may contain only the organic compound. Alternatively, the light-emitting layer may contain a host material and a guest material. The host material is preferably the organic compound as described below.

The host material is a major component of the light-emitting layer. The major component can be defined as a component that occupies most of the weight of the light-emitting layer. The guest material is a minor component of the light-emitting layer. The light-emitting layer may further contain a so-called assist dopant.

The luminescent center of the light-emitting layer has three major examples.

FIG. 7 is an illustration showing the highest occupied molecular orbital (HOMO), lowest unoccupied molecular orbital (LUMO), and luminescent center of each of the host and guest materials.

Examples 4 to 6 of the luminescent center of the light-emitting layer are shown in FIG. 7. An upper portion of this figure is close to the vacuum level. For each example, the HOMO and LUMO of the host material are represented by a solid-line rectangle and the HOMO and LUMO of the host material are represented by dotted lines. A hatched portion of each example is the luminescent center of the light-emitting layer. The emission intensity of the light-emitting layer varies in the thickness direction thereof. A region with particularly high emission intensity is referred to as a luminescent center. In FIG. 7, the horizontal direction of each rectangle is the thickness direction of the light-emitting layer and the right side and left side of the rectangle are the cathode side and anode side, respectively, of the rectangle.

For Example 4, the LUMO of the guest material is lower (more far from the vacuum level, that is, deeper) than the LUMO of the host material. When a voltage is applied to the light-emitting layer, electrons injected from the LUMO of an electron transport layer are trapped in the guest material. Therefore, the light-emitting layer is of an electron trap type and the luminescent center is located close to the electron transport layer.

For Example 5, the LUMO of the guest material is lower than the LUMO of the host material and the HOMO of the guest material is higher than the HOMO of the host material. When a voltage is applied to the light-emitting layer, electrons injected from the LUMO of the electron transport layer are trapped in the guest material and holes injected from the HOMO of a hole transport layer are also trapped in the guest material. Therefore, the light-emitting layer is of a double electron trap type and the luminescent center is located at the thicknesswise center of the light-emitting layer.

For Example 6, the HOMO of the guest material is higher than the HOMO of the host material. When a voltage is applied to the light-emitting layer, holes injected from the HOMO of the hole transport layer are trapped in the guest material. Therefore, the light-emitting layer is of a hole trap type and the luminescent center is located close to the hole transport layer.

Luminescence occurs in the whole of the light-emitting layer. The position of the luminescent center varies depending on the relationship between the HOMOs and LUMOs of the host and guest materials as described above with reference to Examples 4 to 6. In the case of using an optical resonator structure, it is important to take the luminescent center of the light-emitting layer into consideration when the optical path L from the light-emitting layer to the reflective surface. The position of the luminescent center can be specified if the structures of the host and guest materials are determined.

The interface between the light-emitting layer and the cathode or anode or the luminescent center of the light-emitting layer may be used as a reference to determine the optical path L.

In this embodiment, a preferred example of the organic compound, which is contained in the organic light-emitting device, is an aromatic compound containing a five-membered ring. That is, a preferred organic compound used herein is an aromatic compound containing a five-membered ring.

The electron levels of the HOMO and LUMO become lower (become deeper or move away from the vacuum level) due to the strong action of electron attraction. Therefore, the organic compound is preferably used because the organic compound serves as an electron trap type of luminescent material.

A luminescent material trapping electrons or holes can efficiently confine charges and therefore prevent the charges from leaking into a transport layer. This leads to an increase in emission efficiency and an increase in device life.

A technique for designing a preferred organic compound is described below.

A quantum chemical calculation is used to provide the preferred organic compound and is useful in designing a novel organic compound.

Emission properties of an organic compound (material) probably depend on the electron state of the material. The color of light is expressed in the form of a spectrum resulting from the transition of a molecule from an electronically excited state back to the electronic ground state.

The quantum chemical calculation is one of computational chemical approaches and is used to predict molecular properties. Examples of the quantum chemical calculation include a molecular orbital theory (MOT) and a density functional theory (DFT).

Details of these theories are described in Szabo and Ostlund, *Modern Quantum Chemistry*, University of Tokyo Press, 1991 and Parr and Yang, *Density-Functional Theory of Atoms and Molecules*, Springer-Verlag, 1996.

In order to understand the expression mechanism of the color and color purity (emission spectrum) of the light emitted from a material and in order to design a desired material, it is important to understand the molecular structure and molecular vibration of a material in the electronic ground state or an excited state.

For, for example, a fluorescent material for use in organic light-emitting devices, the light emitted by the de-excitation of molecules of the fluorescent material from an excited singlet (S1) state to the ground singlet (S0) state is used. Therefore, the molecular structure and molecular vibration of the fluorescent material in these electronic states need to be investigated.

Figure 8:
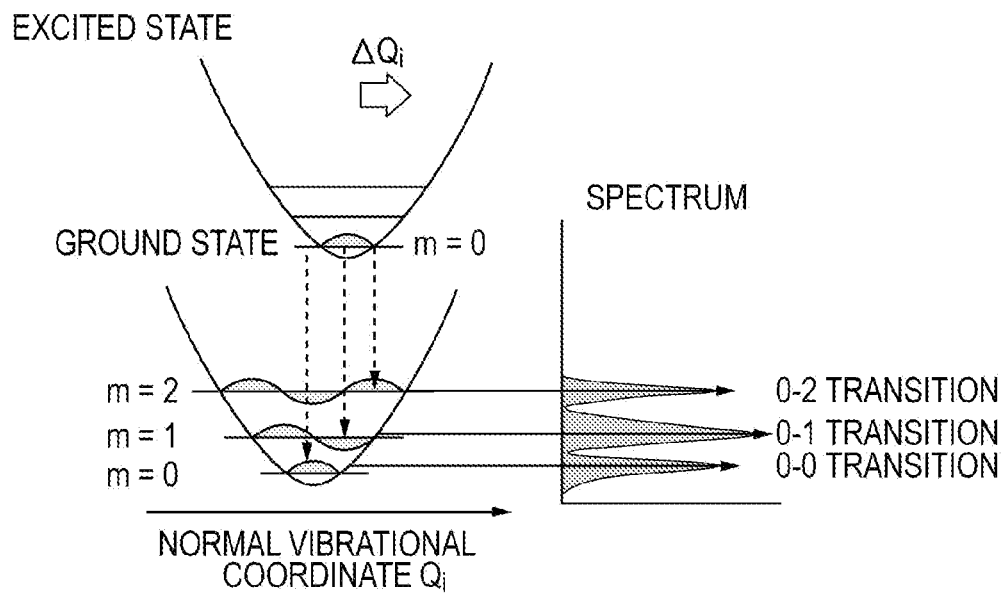
FIG. 8 is an illustration showing the vibrational progression of an emission spectrum due to a normal vibrational mode.

An emission spectrum exhibits a pattern called vibrational progression, which results from the change in molecular structure due to the transition from an electronically excited state to the electronic ground state. A molecule consisting of N atoms usually has (3N-6) normal vibrational modes (or (3N-5) normal vibrational modes when the molecule is linear). The change in structure of the molecule can be divided into components of normal vibrational coordinates corresponding to the normal vibrational modes. When the shift of each normal vibrational coordinate is small, the energy change of the molecular structure can be approximated to be a harmonic oscillator. On the basis of this approximation, the vibrational progression of an emission spectrum due to a normal vibrational mode (i) is as described below with reference to FIG. 8.

The intensity of an emission spectrum in which (3N-6) normal vibrational modes are all formulated is given by the following proportion as described in Yi Jing Yan and Shaul Mukamel, *J. Chem. Phys.*, 85, 5908 (1986):

$$I(\nu_{em}) \propto \nu_{em}^3 \cdot \int dt \, \exp[i(\nu_{em}-\nu_{00})t - g(t)] \cdot \sigma_t(t) \quad (2)$$

wherein I is the intensity of the emission spectrum, $\nu_{00}$ is the wave number of 0-0 transition, $\nu_{em}$ is the wave number of emission, and g(t) is a function of a time domain showing inhomogeneous broadening and is given by the following equation:

$$g(t) = \Delta \nu_{in}^2 t^2 \quad (3).$$

In Proportion 2, $\Delta\nu_{in}$ is the full width at half maximum of a spectrum due to inhomogeneous broadening and varies depending on the environment where the molecule is placed; hence, $\Delta\nu_{in}$ is determined by experiment. In Proportion 2, $\sigma_t(t)$ is given by the following equation:

$$\sigma_t(t) = \exp\left\{ S_i \frac{\exp(i\omega_i t) - 1 + \exp(-\beta\hbar\omega_i)[\exp(-i\omega_i t) - 1]}{1 - \exp(-\beta\hbar\omega_i)} \right\} \quad (4)$$

wherein $\omega_i$ is the frequency of a normal vibrational mode; $\beta = 1/kT$, where k is the Boltzmann constant and T is temperature; and $S_i$ is the Huang-Rhys factor of the normal vibrational mode (i) (i is equal to 1 to 3N-6 and N is the number of atoms forming the molecule) and is given by the following equation:

$$S_i = \frac{\lambda_{vib,i}}{h\nu_i} = \frac{2\pi^2 \nu_i \Delta Q_i^2}{h} \quad (5)$$

wherein h is the Planck constant, $\nu_i$ is the wave number of the normal vibrational mode (i), and $\Delta Q_i$ is the shift of a normal vibrational coordinate between an excited state and the ground state.

Figure 9:
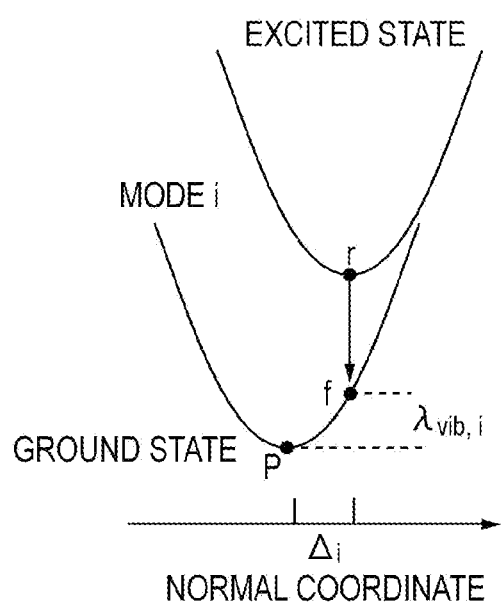
FIG. 9 is an illustration showing the shift of a normal vibrational coordinate between an excited state and the ground state.

FIG. 9 illustrates Equation 5.

As is clear from FIG. 9 and Equation 5, the Huang-Rhys factor $S_i$ is given by normalizing the energy $\lambda\nu_{ib,i}$ of the shift of the normal vibrational mode (i) between an excited state and the ground state by the energy of the normal vibrational mode (i). Therefore, the Huang-Rhys factor $S_i$ shows the magnitude of the shift of the molecular structure between the ground state and an excited state in the normal vibrational mode (i). The fact that a Huang-Rhys factor in a normal vibrational mode is large means that the spectral broadening due to the Huang-Rhys factor is large. The molecule, which consists of N atoms, has the (3N-6) normal vibrational modes (or (3N-5) normal vibrational modes when the molecule is linear) as described above and therefore has (3N-6) Huang-Rhys factors different in magnitude from each other depending on the normal vibrational modes.

In order to digitize the broadening of an emission spectrum, we herein define a profile factor (PF) using a Huang-Rhys factor given by Equation 5 as given by the following equation:

$$PF = \sum_{k \in R} S_k / N_{basis} \quad (6)$$

wherein R in the summation is a region for a specific normal vibrational mode of the molecule and $N_{basis}$ is the number of atoms contained in a specific portion of the molecule.

As is known, the range of vibrational energy is classified as below.
C-H stretching: 3,000 cm$^{-1}$ or more
C-C ring stretching: 1,400 to 1,660 cm$^{-1}$
C-H in-plane bending and ring stretching: 1,000 to 1,300 cm$^{-1}$
C-H out-of-plane bending: 1,000 cm$^{-1}$ or less C-H stretching, which is high in frequency, and C-H out-of-plane bending, which is high in frequency, have no significant effects on the waveform of an emission spectrum. C-C ring stretching is most influential and C-H in-plane bending and ring stretching are also influential. Therefore, a normal vibrational mode is within the range of 1,300 to 1,680 cm$^{-1}$ (principally a C-H in-plane stretching mode and/or a C-H in-plane bending mode). Although the range is preferably 1,300 to 1,680 cm$^{-1}$, coherent values can be obtained when the range is 1,200 to 1,700 cm$^{-1}$.

For the luminescent material used herein, R is defined as a normal vibrational mode (principally a C-H in-plane stretching mode or a C-H in-plane bending mode) within the range of 1,300 to 1,680 cm$^{-1}$ and $N_{basis}$ is defined as the number of atoms, other than those forming a substituent and hydrogen atoms, in the framework of an organic compound.

The PF shows the degree of the "shift" of a molecule, in a normal vibrational mode within the above range, between the ground state and an excited state and therefore is defined as a value corresponding to an amount determined by digitizing the broadening of an emission spectrum due to the shift.

In the calculation of the PF, $N_{basis}$ is the number of the framework atoms, in which transition orbitals are principally distributed in an excited state, and excludes the number of the substituent atoms, in which transition orbitals are hardly present. The term "excited state" as used herein means the first singlet excited state. The term "transition orbital" as used herein means the highest occupied molecular orbital (HOMO) or lowest unoccupied molecular orbital (LUMO).

The calculation has been verified for validity in such a manner that calculated values and measurements obtained from an organic compound with a substituent in which a transition orbital is hardly distributed and an organic compound with no substituent.

A procedure of the calculation is as described below. Commercially available software programs, Gaussian 03 Revision D.01 and Turbomole 5.9.1, for electronic state calculation are used to calculate the structure of a molecule in the electronic ground state or an electronically excited state and normal vibrational modes of the molecule. A quantum chemical calculation used is a density functional theory and B3LYP was used for functional. For basis function, 6-31G(d) is used in Gaussian 03 Revision D.01 and def-SV(P) is used in Turbomole 5.9.1. The data calculated from the structure of the molecule in the electronic ground state or an electronically excited state and the normal vibrational modes of the molecule by these software programs is used to calculate a Huang-Rhys factor, an emission spectrum, and a PF. The full width at half maximum $\Delta v_{in}$ of a spectrum due to inhomogeneous broadening is set to 600 cm$^{-1}$, which is a value suitable for well reproducing an experiment spectrum.

Gaussian 03 Revision D.01; M. J. Frisch, G. W. Trucks, H. B. Schlegel, G. E. Scuseria, M. A. Robb, J. R. Cheeseman, J. A. Montgomery, Jr., T. Vreven, K. N. Kudin, J. C. Burant, J. M. Millam, S. S. Iyengar, J. Tomasi, V. Barone, B. Mennucci, M. Cossi, G. Scalmani, N. Rega, G. A. Peterson, H. Nakatsuji, M. Hada, N. Ehara, K. Toyota, R. Fukuda, J. Hasegawa, M. Ishida, T. Nakajima, Y. Honda, O. Kitao, H. Nakai, M. Klene, X. Li, J. E. Knox, H. P. Hratchian, J. B. Cross, V. Bakken, C. Adamo, J. Jaramillo, R. Gomoperts, R. E. Stratmann, O. Yazyev, A. J. Austin, R. Cammi, C. Pomelli, J. W. Ochterski, P. Y. Ayala, K. Morokuma, G. A. Voth, P. Salvador, J. J. Dannenberg, V. G. Zakrzewski, S. Dapprich, A. D. Daniels. M. C. Strain, O. Farkas, D. K. Malick, A. D. Rabuck, K. Raghavachari, J. B. Foresman, J. V. Ortiz, Q. Cui, A. G. Baboul, S. Clifford, J. Cioslowski, B. B. Stefanov, G. Liu, A. Liashenko, P. Piskorz, I. Komaromi, R. L. Martin, D. J. Fox, T. Keith, M. A. Al-Laham, C. Y. Peng, A. Nanayakkara, M. Challacombe, P. M. W. Gill, B. Johnson, W. Chen, M. W. Wong, C. Gonzalez, and J. A. Pople; Gaussian, Inc., Wallingford Conn., 2004

An emission spectrum in which the height ratio of a first vibrational peak to a second vibrational peak varies is obtained from the calculation. In the case of using an optical resonator structure in a light-emitting device, the percent of a light portion that is attenuated without being extracted significantly depends on the height ratio of a first vibrational peak to a second vibrational peak. Therefore, the height ratio of a first vibrational peak to a second vibrational peak is important in designing molecules.

The height ratios and area ratios of first vibrational peaks to second vibrational peaks are described below.

FIGS. 10 to 13 are graphs illustrating emission spectra each having a first vibrational peak and a second vibrational peak.

Figure 10:
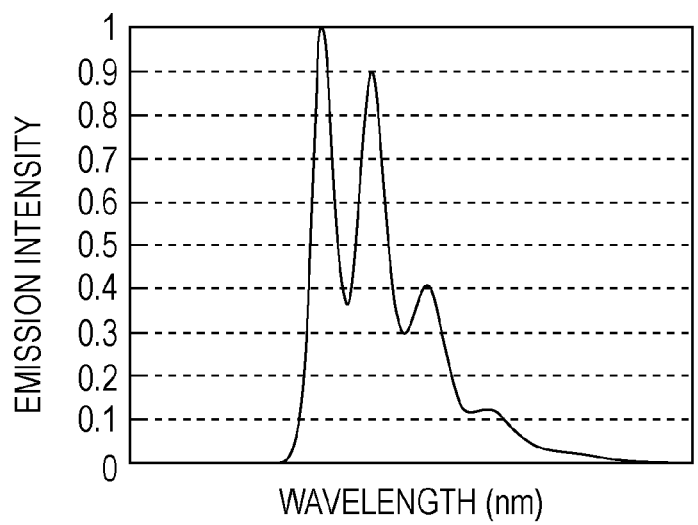
FIG. 10 is a graph illustrating an emission spectrum having a first vibrational peak and a second vibrational peak.
Figure 11:
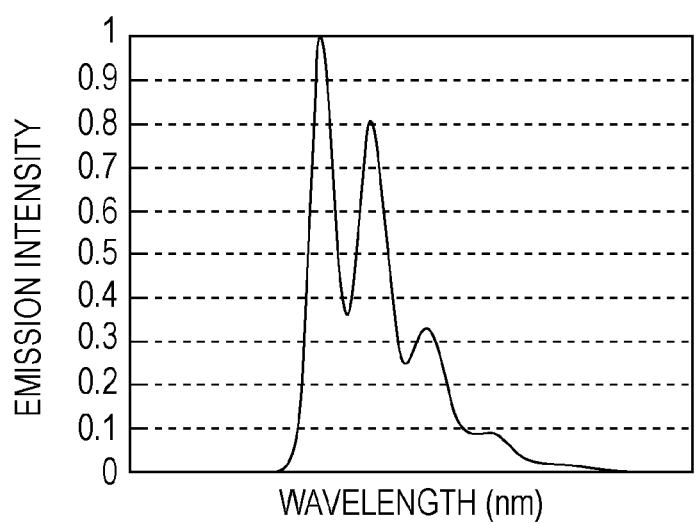
FIG. 11 is a graph illustrating an emission spectrum having a first vibrational peak and a second vibrational peak.
Figure 12:
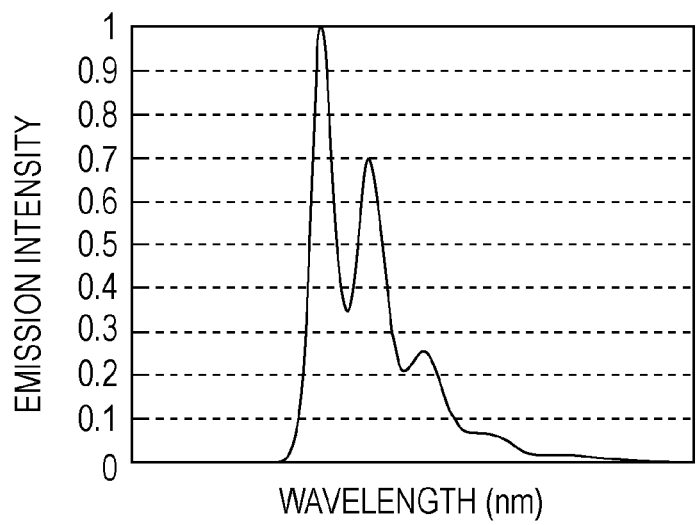
FIG. 12 is a graph illustrating an emission spectrum having a first vibrational peak and a second vibrational peak.
Figure 13:
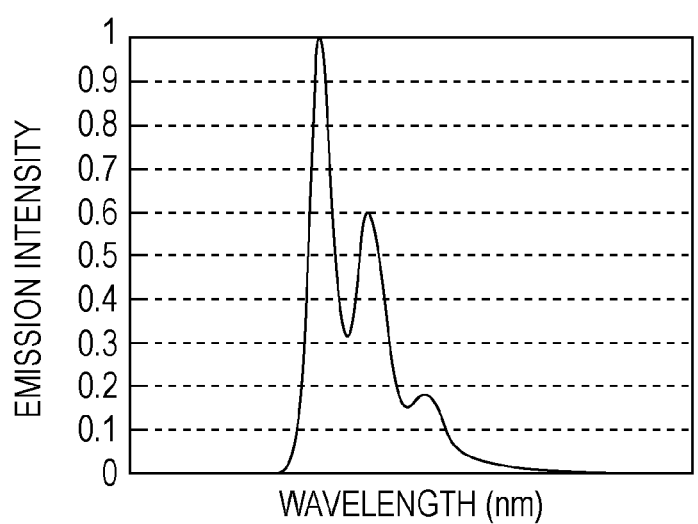
FIG. 13 is a graph illustrating an emission spectrum having a first vibrational peak and a second vibrational peak.

With reference to FIG. 10, the height ratio of the second vibrational peak to the first vibrational peak is 0.9. With reference to FIG. 11, the height ratio of the second vibrational peak to the first vibrational peak is 0.8. With reference to FIG. 12, the height ratio of the second vibrational peak to the first vibrational peak is 0.7. With reference to FIG. 13, the height ratio of the second vibrational peak to the first vibrational peak is 0.6.

Table 2 summarizes the heights and areas of the first and second vibrational peaks shown in FIGS. 10 to 13.

Results obtained from the spectra shown in FIGS. 10 to 13 are shown in Table 2 in that order.

TABLE 2

| Height | | Area | |
|---|---|---|---|
| First vibrational peaks | Second vibrational peaks | First vibrational peaks | Second vibrational peaks |
| 1.0 | 0.9 | 35 | 65 |
| 1.0 | 0.8 | 43 | 57 |

TABLE 2-continued

| Height | | Area | |
|---|---|---|---|
| First vibrational peaks | Second vibrational peaks | First vibrational peaks | Second vibrational peaks |
| 1.0 | 0.7 | 54 | 46 |
| 1.0 | 0.6 | 62 | 38 |

These results show that the second vibrational peak of each spectrum in which the first vibrational peak is greater than 0.7 has an area of not less than 50.

It is preferred that an organic compound with no second vibrational peak can be designed. However, organic compounds necessarily have carbon-carbon vibrational modes. Therefore, it is preferable for a high-efficiency liquid ejection device to have a first vibrational peak with an area greater than that of a second vibrational peak. The intensity ratio of the second vibrational peak to the first vibrational peak is 0.7 or less. The PF given by the intensity ratio is 0.02 or less. The first vibrational peak has a full width at half maximum of 30 nm or less. An organic light-emitting device having an optical resonator structure satisfying these values has high color purity and a preferred spectral form.

The inventors have found that if a material with a PF of 0.02 or less is designed, calculation and measurement show that this material has an emission spectrum with a first vibrational peak and a second vibrational peak. In this material, the intensity ratio of the second vibrational peak to the first vibrational peak is 0.7 or less and the first vibrational peak has a narrow full width at half maximum of 30 nm or less. Although there is a difference of about ±5 to ±10 nm between the calculated and measured emission spectra of this material, the calculated and measured emission spectra thereof have substantially the same form.

The molecular design of a material allows this material to have a maximum emission peak having a desired wavelength and high intensity as described above.

The organic compound of this embodiment has high quantum efficiency and a narrow full width at half maximum and therefore emits light which is suitable for blue liquid ejection devices and which has good color purity. The use of the organic compound thereof in a light-emitting device having an optical resonator structure reduces a light portion that is attenuated and allows this liquid ejection device to have high light extraction efficiency, external quantum efficiency, and color purity.

An organic light-emitting device according to a second embodiment of the present invention will now be described.

The organic light-emitting device includes an anode, a cathode, and organic compound layers arranged therebetween, the anode and cathode being a pair of electrodes. The organic light-emitting device is a type of device containing a luminescent material which is disposed between a pair of electrodes, which is an organic compound, and which emits light.

When a light-emitting layer is one of the organic compound layers, the light-emitting layer may be made of or may contain an organic compound according to the present invention.

When the light-emitting layer contains the organic compound according to the present invention, the organic compound according to the present invention may be a major or minor component of the light-emitting layer.

The term "major component" as used herein means one of all organic compounds contained in the light-emitting layer, the one having a higher content on a weight or molar basis. The term "minor component" as used herein means one of all the organic compounds therein, the one having a lower content on a weight or molar basis.

A material that is a major component may be referred to as a host material.

A material that is a minor component may be referred to as a dopant (guest) material, an emission-assisting material, or an electron injection material.

When a luminescent material designed herein is used as a guest material, the content of the guest material in the light-emitting layer is preferably 0.01 to 20 weight percent and more preferably 0.5 to 10 weight percent.

When the light-emitting layer contains the guest material and a host material that transports carriers, a light-emitting process includes steps below.
  1. Transporting electrons in the light-emitting layer.
  2. Producing excitons in the host material.
  3. Transferring excitation energy between molecules of the host material.
  4. Transferring excitation energy from the host material to the guest material.

In the above steps, energy transfer and/or emission occurs competitively with deactivation.

For the enhancement of the emission efficiency of the organic light-emitting device, a luminescent center material (for example, the guest material) preferably has a large emission quantum yield. It is a big issue whether energy can be efficiently transferred between the host and guest materials. A cause of the reduction of emission during conduction is not clear at present and is probably the change in the luminescent center material itself or the change in circumstances of the luminescent center material due to molecules surrounding the luminescent center material.

The organic light-emitting device is further described below in detail.

The organic light-emitting device, which includes the anode, the cathode, and the organic compound layers, contains the organic compound according to the present invention.

The organic light-emitting device may further include another organic compound layer disposed between the anode and the cathode in addition to that organic compound layers.

The organic light-emitting device may include two or more organic compound layers, including that organic compound layers, disposed between the anode and cathode. In this case, the organic light-emitting device is referred to as a multilayer-type organic light-emitting device.

Preferred examples of the multilayer-type organic light-emitting device are described below.

A first example of the multilayer-type organic light-emitting device includes an anode, light-emitting layer, and cathode arranged on a substrate in that order. The first example is effective in using an organic compound having a hole transport capability, an electron transport capability, and a light-emitting capability or effective in using organic compounds each having a corresponding one of these capabilities in combination.

A second example of the multilayer-type organic light-emitting device includes an anode, hole transport layer, electron transport layer, and cathode arranged on a substrate in that order. The second example is effective in using a luminescent material having one or both of a hole transport capability and an electron transport capability in these layers in combination with a material having no light-emitting capability but a hole or electron transport capability. The hole or electron transport layer functions as a light-emitting layer.

A third example of the multilayer-type organic light-emitting device includes an anode, hole transport layer, light-emitting layer, electron transport layer, and cathode arranged on a substrate in that order. In the third example, a carrier transport function and a light-emitting function are separated. Organic compounds each having a hole transport capability, an electron transport capability, or a light-emitting capability can be appropriately used in combination in the third example. The third example has a high degree of freedom in selecting materials and various organic compounds with different emission wavelengths can be used; hence, light of various colors can be emitted from the third example. The emission efficiency of the third example can be increased in such a manner that carriers or excitons are effectively confined in the light-emitting layer.

A fourth example of the multilayer-type organic light-emitting device includes an anode, hole injection layer, hole transport layer, light-emitting layer, electron transport layer, and cathode arranged on s substrate in that order. This configuration is effective in improving the adhesion between the anode and the hole transport layer, effective in improving the injection of holes, and effective in reducing the voltage applied between the anode and the cathode.

A fifth example of the multilayer-type organic light-emitting device includes an anode, hole transport layer, light-emitting layer, hole/exciton-blocking layer, electron transport layer, and cathode arranged on a substrate in that order. The hole/exciton-blocking layer is disposed between the light-emitting layer and the electron transport layer so as to prevent holes from migrating toward the cathode. The use of an organic compound with an extremely high ionization potential in the hole/exciton-blocking layer is effective in increasing the emission efficiency of the fifth example. The hole/exciton-blocking layer and the hole transport layer may be replaced with a hole transport layer and an electron injection layer, respectively. This is effective in improving the adhesion between the cathode and the electron transport layer, effective in improving the injection of electrons, and effective in reducing the voltage applied between the anode and the cathode.

The organic light-emitting device has a light-emitting region corresponding to a region of the light-emitting layer.

The first to fifth examples of the multilayer-type organic light-emitting device have only a basic configuration; hence, the organic light-emitting device is not limited to the first to fifth examples thereof. The organic light-emitting device may include, for example, an insulating layer disposed between an electrode and an organic layer, an adhesive or interference layer, and/or an electron or hole transport layer including two sub-layers with different ionization potentials.

The organic light-emitting device has a luminescent center. The luminescent center may be located at the center of the light-emitting layer, a position which is in the light-emitting layer and which is close to the hole transport layer, a position which is in the light-emitting layer and which is close to the electron transport layer, or another position. The luminescent center, the light-emitting layer, and one or more mirror-reflective films, such as electrodes, disposed on one or both surfaces of the light-emitting layer form an optical microresonator. Light resonated in the optical microresonator is amplified and can be emitted so as to have a wavelength corresponding to the resonant frequency thereof.

For example, a semitransparent reflective layer is formed on a substrate and a transparent conductive layer is formed on the semitransparent reflective layer. Such a layered structure as described in one of the first to fifth examples is provided on the transparent conductive layer. A portion of the light emitted from the light-emitting layer passes through the semitransparent reflective layer to travel toward a transparent base and a remaining portion of the light emitted from the light-emitting layer is reflected by the semitransparent reflective layer toward the light-emitting layer. Therefore, the semitransparent reflective layer and an electrode disposed on the back of the light-emitting layer cooperate to act as an optical resonator.

In this case, the thickness of each layer needs to be designed so as to satisfy the following equation:

$$nd = (2N-1)\lambda/4$$

wherein n is the refractive index of the layer, d is the distance (in nm) from the luminescent center to the layer, $\lambda$ is the peak wavelength of emitted light, and N is a positive integer.

The organic light-emitting device can be used in the form of any one of the first to fifth examples. There are no restrictions on materials used to form an optical resonator structure except the refractive index thereof.

In the organic light-emitting device, the following compound can be used in combination with the above-mentioned organic compound, that is, a luminescent material: a known low- or high-molecular weight hole-transporting/injecting compound, luminescent compound, or electron-transporting/injecting compound.

Examples of these compounds are described below.

The hole-transporting/injecting compound preferably has high hole mobility such that holes can be readily injected from the anode and the injected holes can be transported to the light-emitting layer. Examples of the hole-transporting/injecting compound, which has a low or high molecular weight, include, but are not limited to, triarylamine derivatives, phenylenediamine derivatives, stilbene derivatives, phthalocyanine derivatives, porphyrin derivatives, polyvinylcarbazoles, polythiophenes, and other conductive polymers.

Examples of the host material include, but are not limited to, condensed ring compounds such as fluorene derivatives, naphthalene derivatives, anthracene derivatives, pyrene derivatives, carbazole derivatives, quinoxaline derivatives, and quinoline derivatives; organoaluminum complexes such as tris(8-quinolinolato) aluminum; organozinc complexes; and polymeric derivatives such as triphenylamine derivatives, polyfluorene derivatives, and polyphenylene derivatives.

The electron-transporting/injecting compound can be arbitrarily selected from materials that are capable of readily injecting electrons from the cathode and capable of transporting the injected electrons to the light-emitting layer and is determined in consideration of the balance between the hole mobility of the hole-transporting/injecting compound and that of the electron-transporting/injecting compound. Examples of the electron-transporting/injecting compound include, but are not limited to, oxadiazole derivatives, oxazole derivatives, pyrazine derivatives, triazole derivatives, triazine derivatives, quinoline quinoxaline derivatives, phenanthroline derivatives, and organoaluminum complexes.

A material for forming the anode preferably has a large work function. Examples of the anode-forming material include metals such as gold, platinum, silver, copper, nickel, palladium, cobalt, selenium, vanadium, and tungsten; alloys of these metals; metal oxides such as tin oxide, zinc oxide, indium oxide, indium tin oxide (ITO), and indium zinc oxide; and conductive polymers such as polyaniline, polypyrrole, and polythiophene. These materials may be used alone or in combination. The anode may have a single-layer or multi-layer structure.

A material for forming the cathode preferably has a small work function. Examples of the cathode-forming material include alkali metals such as lithium; alkaline-earth metals such as calcium; metals such as aluminum, titanium, manganese, silver, lead, and chromium; alloys, such as magnesium-silver alloys, aluminum-lithium alloys, aluminum-magnesium alloys, containing these metals; and metal oxides such as ITO. These materials may be used alone or in combination. The cathode may have a single-layer or multilayer structure.

Examples of a substrate used for the organic light-emitting device include, but are not limited to, metal substrates; opaque substrates such as ceramic substrates; transparent substrate made of glass, quartz, plastic, or the like; color filter films; fluorescent color conversion filter films; and dielectric reflective films.

In order to protect the organic light-emitting device from oxygen, moisture, or the like, a protective layer and/or a sealing layer may be provided on the organic light-emitting device. Examples of the protective layer include inorganic material layers such as diamond thin-films, metal oxide films, and metal nitride films; polymeric films such as fluorocarbon films, polyethylene films, silicone films, and polystyrene films; and photocurable resin films. Alternatively, the organic light-emitting device may be coated with glass or metal, covered with a gas barrier film, or packaged with an appropriate sealing resin.

In the organic light-emitting device, a layer containing the organic compound according to the present invention and a layer containing another organic compound are by the following process in general: a vacuum vapor deposition process; an ionization vapor deposition process; a sputtering process; a plasma process; or a known coating process, such as a spin coating process, a dipping process, a casting process, a Langmuir-Blodgett (LB) process, or an ink jet process, using an appropriate solvent. A layer formed by a vacuum vapor deposition process, a solution-coating process, or a similar process has good temporal stability because crystallization or the like is unlikely to occur in this layer. A coating process may be used in combination with an appropriate binder resin used to form a film.

Examples of the binder resin include, but are not limited to, polyvinylcarbazoles, polycarbonates, polyesters, ABS resins, acrylic resins, polyimides, phenol resins, epoxy resins, silicone resins, and urea resins. These resins may be homopolymers or copolymers and may be used alone or in combination. The binder resin may be used in combination with a known additive such as a plasticizer, an oxidation inhibitor, or an ultraviolet absorber.

The organic light-emitting device is applicable to products required to have high energy efficiency and high brightness. Applications of the organic light-emitting device include light sources for display apparatuses, lighting apparatuses, and printers and backlights for liquid crystal displays.

The display apparatuses can be used for light-weight flat panel displays having high energy efficiency and high visibility. The display apparatuses can be used as image display apparatuses such as PC monitors, televisions, and advertising media. Alternatively, the display apparatuses may be used for display sections of image pickup apparatuses, such as digital still cameras and digital video cameras, including image-pickup units. Images are displayed on the display sections.

The display apparatuses may be used for operation display sections of electrophotographic image-forming apparatuses such as laser beam printers and copiers.

The display apparatuses may be used as light sources used to form latent images on photoreceptors in electrophotographic image-forming apparatuses such as laser beam printers and copiers. A latent image can be formed in such a manner that a plurality of independently addressable organic light-emitting devices are arrayed (or linearly arranged) and desired light is applied to a photoconductive drum. The use of the organic light-emitting device is effective in reducing a space for storing a light source, a polygonal mirror, various optical lenses, and the like.

For lighting apparatuses and backlights, energy-saving effects can be expected due to the organic light-emitting device. The organic light-emitting device can be used as a flat light source.

The color of light can be controlled in such a manner that a color filter film, a fluorescent color conversion filter film, and/or a dielectric reflective film is provided on or above a substrate carrying the organic light-emitting device. The emission of light can be controlled in such a manner that a thin-film transistor (TFT) is provided on a substrate and connected to the organic light-emitting device. A lighting apparatus can be formed in such a manner that a plurality of organic light-emitting devices identical in configuration to the organic light-emitting device are arranged in a matrix pattern, that is, in the in-plane direction.

A display apparatus 1 according to a third embodiment of the present invention will now be described. The display apparatus includes a plurality of organic light-emitting devices 24 identical in configuration to the organic light-emitting device according to the first or second embodiment and also includes units supplying electric signals to the organic light-emitting devices 24. Taking active matrix addressing as an example, the display apparatus 1 is described below in detail with reference to FIGS. 14 to 17.

Figure 14:
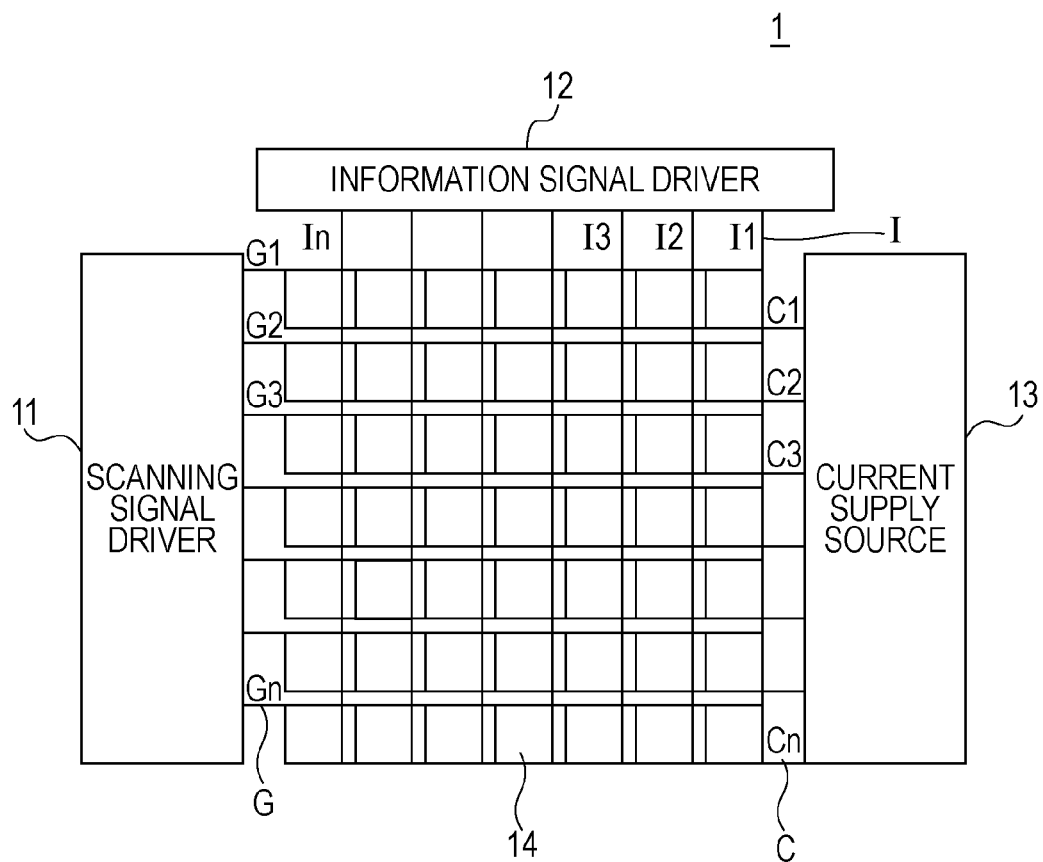
FIG. 14 is a schematic view of a display apparatus including organic light-emitting devices and units that supply electric signals to the organic light-emitting devices.

FIG. 14 is a schematic view of the display apparatus 1, which includes the organic light-emitting devices 24 and the units.

Figure 15:
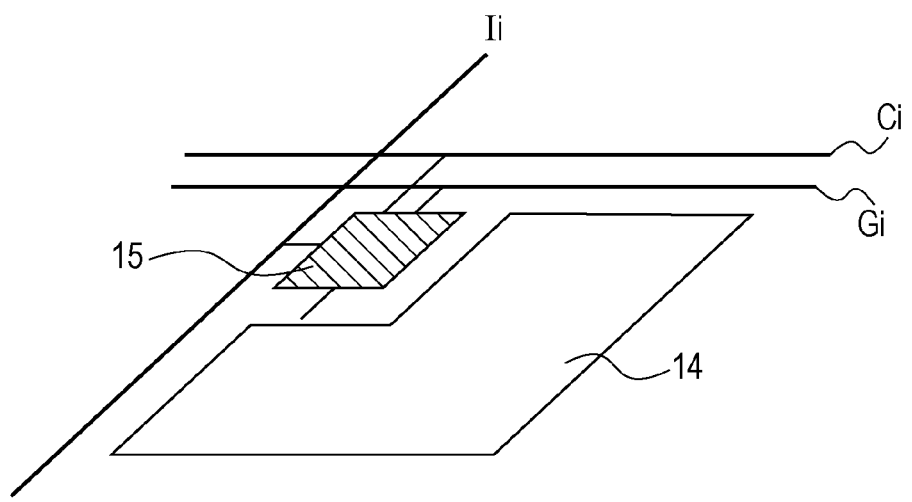
FIG. 15 is a schematic view of a pixel circuit connected to a pixel, an information signal line, a gate selection line, and a current supply line.

FIG. 15 is a schematic view of one of pixel circuits 15 connected to pixels 14, information signal lines I, gate selection lines G, and current supply lines C.

The units, which supply electric signals to the organic light-emitting devices 24, correspond to a scanning signal driver 11, an information signal driver 12, and current supply source 13 shown in FIG. 14 and the pixel circuits 15 shown in FIG. 15.

With reference to FIG. 14, the scanning signal driver 11, the information signal driver 12, and the current supply source 13 are arranged in the display apparatus 1 and connected to the gate selection lines G, the information signal lines I, and the current supply lines C, respectively. The pixel circuits 15 are located at intersections of the gate selection lines G and the information signal lines I as shown in FIG. 5. The pixels 14 include the organic light-emitting devices 24 and are arranged so as to correspond to the pixel circuits 15. The organic light-emitting devices 24 are shown in the form of light spots. The organic light-emitting devices 24 may be commonly connected to an upper electrode or may be separately connected to upper electrodes.

The scanning signal driver 11 sequentially selects the gate selection lines G1, G2, G3, . . . , Gn. In synchronization with this operation, an image signal is applied to each pixel circuit 15 from the information signal driver 12 through a corresponding one of the information signal lines I1, I2, I3, . . . , In.

Figure 16:
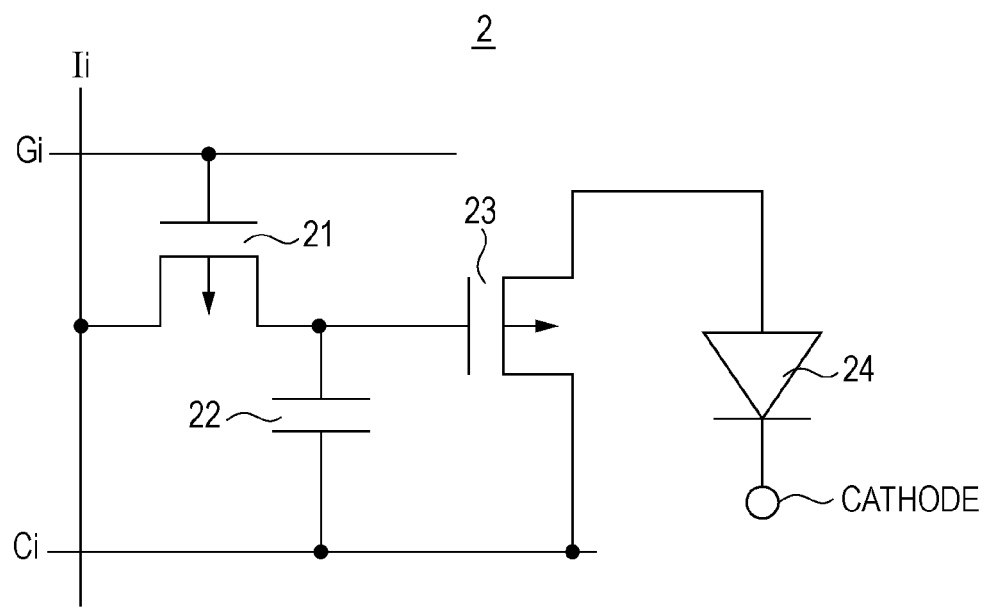
FIG. 16 is a diagram of a circuit forming a pixel.

The operation of the pixels 14 is described below. FIG. 16 is a diagram of a circuit 2 forming each pixel 14, which is disposed in the display apparatus 1 as shown in FIG. 14. With reference to FIG. 16, a second thin-film transistor (second TFT) 23 controls a current for causing a corresponding one of the organic light-emitting devices 24 to emit light. In the circuit 2, the application of a selection signal to the gate selection line G1 causes a first thin-film transistor (TFT) 21 to be turned on, whereby an image signal Ii is supplied to a capacitor ($C_{add}$) 22 to determine the gate voltage of a second thin-film transistor (TFT) 23 as shown in FIG. 16. A current is supplied to the corresponding organic light-emitting device 24 through the current supply line Ci depending on the gate voltage of the second TFT 23. The gate voltage of the second TFT 23 is held by the capacitor ($C_{add}$) 2 until the first TFT 21 is scanned and selected next. Therefore, a current flows continuously through the organic light-emitting device 24 until scanning is performed next. This allows the organic light-emitting device 24 to continuously emit light during one frame.

The voltage applied between the electrodes of each organic light-emitting device 24 may be controlled by a thin-film transistor and therefore the organic light-emitting devices 24 can be used in a voltage programming-type display apparatus, which is not shown.

The display apparatus 1 may be a full-color display apparatus. The full-color display apparatus includes a plurality of pixels that can each provide full color emission. Each of these pixels includes a plurality of sub-pixels and may include, for example, three sub-pixels each emitting light of a corresponding one of red, green, and blue. Each of the sub-pixels includes a corresponding one of the organic light-emitting devices.

Figure 17:
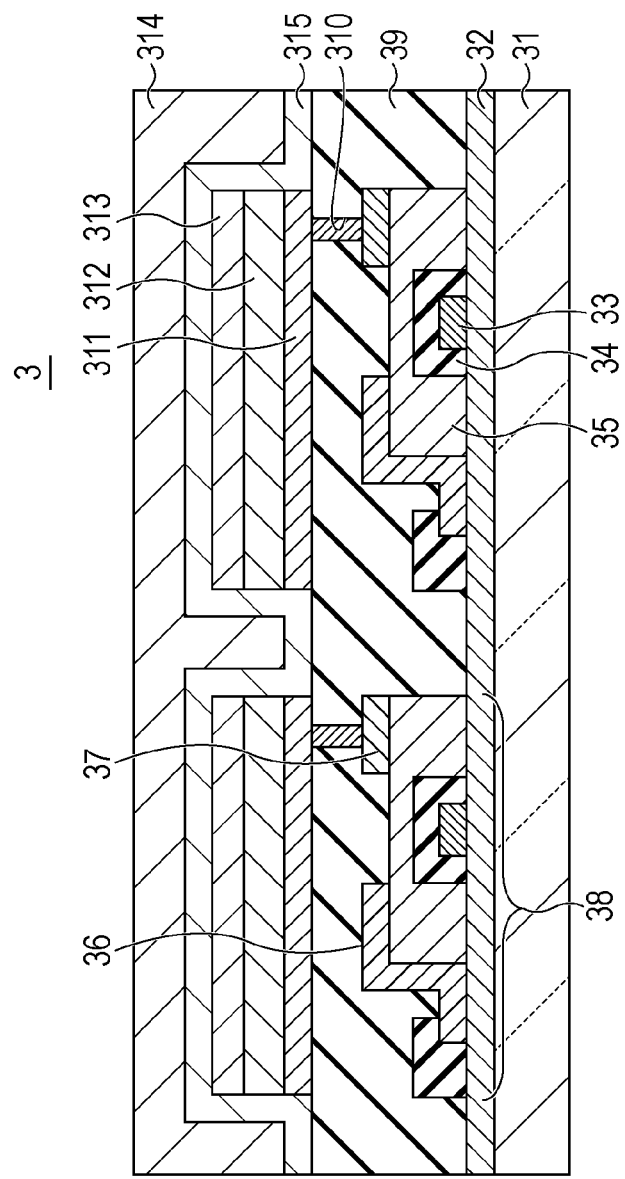
FIG. 17 is a schematic sectional view of a TFT board.

FIG. 17 is a schematic sectional view of an exemplary TFT board 3 used in the display apparatus 1, which is shown in FIG. 14. The configuration of the TFT board 3 is described below in detail with reference to steps of manufacturing the TFT board 3.

In the manufacture of the TFT board 3, which is shown in FIG. 17, a moisture barrier layer 32 for protecting members such as TFTs and organic layers is formed on a substrate 31 made of glass or the like by coating. A material used to form the moisture barrier layer 32 is silicon dioxide, a mixture of silicon dioxide and silicon nitride, or the like. A layer of a metal such as chromium is deposited on the moisture barrier layer 32 by sputtering and then patterned into a predetermined circuit shape, whereby gate electrodes 33 are formed.

A layer of silicon dioxide or the like is deposited over the gate electrodes 33 and the moisture barrier layer 32 by a plasma-enhanced chemical vapor deposition (PECVD) process, a catalytic chemical vapor deposition (CCVD) process, or a similar process and then patterned, whereby gate insulating layers 34 are formed. A layer of silicon is deposited over the gate insulating layers 34 and the moisture barrier layer 32 by a PECVD process or a similar process and then patterned into a shape following the circuit shape, whereby semiconductor layers 35 are formed. The silicon layer may be annealed at a temperature of 290° C. or higher as required in advance of patterning.

Drain electrodes 36 and source electrodes 37 are provided on the semiconductor layers 35, whereby TFTs 38 are fabricated, whereby such a circuit as shown in FIG. 16 is formed. An insulating layer 39 is formed over the TFTs 38. Contact holes (through-holes) 310 are formed in the insulating layer 39 such that the source electrodes 37 are connected to anodes 311, made of a metal, for the organic light-emitting devices.

Organic layers 312 with a single-layer or multilayer structure and cathodes 313 are deposited on the anodes 311 in that order, whereby the TFT board 3 is obtained. In order to prevent the deterioration of the organic light-emitting devices, a first protective layer 314 and/or a second protective layer 315 may be provided over the cathodes 313. The display apparatus 1 includes the organic light-emitting devices and therefore can stably display a high-quality image for a long time when being driven.

In the display apparatus 1, a switching element used is not particularly limited and a single-crystalline silicon substrate, an MIM element, an amorphous silicon substrate, and/or the like can be used.

Organic light-emitting layers with a single-layer or multilayer structure and anode layers are deposited on ITO electrodes in that order, whereby an organic light-emitting display panel can be obtained. The organic light-emitting display panel contains an organic compound according to the present invention and therefore can stably display a high-quality image for a long time when being driven.

For a direction in which light is extracted from each device, an optical resonator structure may be maintained. The device may be of a bottom emission type (light is extracted from the substrate side of the device) or a top emission type (light is extracted from the opposite side of the substrate).

EXAMPLES

The present invention is further described below in detail with reference to examples. The present invention is, not limited to the examples.

Example 1

In this example, Organic Compound 1 having the following formula was designed and calculated for spectrum:

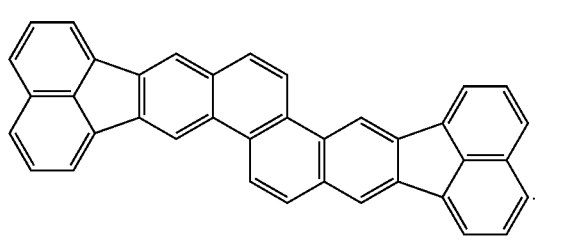

(1)

The PF of Organic Compound 1 was calculated from Equation 6, wherein a wave number (1,300 to 1,670 cm$^{-1}$) corresponding to the in-plane stretching mode of carbon atoms was specified for R in the summation and the number of carbon atoms contained in a molecule of Organic Compound 1 was specified for $N_{basis}$.

Figure 18:
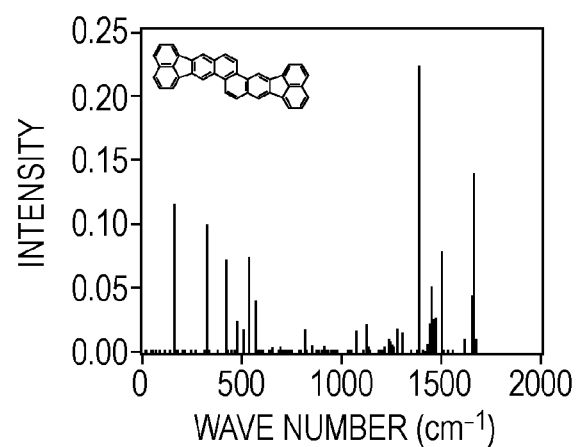
FIG. 18 is a graph illustrating the calculated Huang-Rhys factor of Organic Compound 1.
Figure 19:
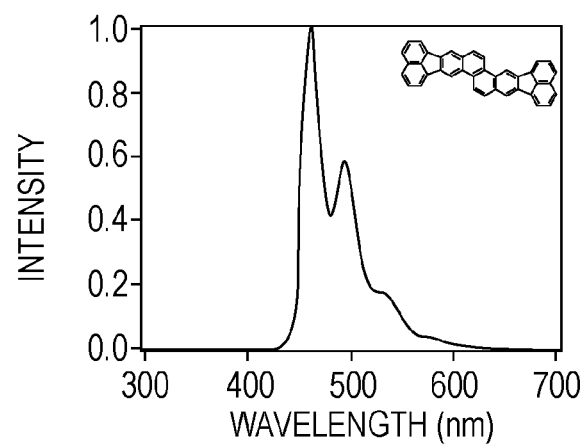
FIG. 19 is a graph illustrating the calculated emission spectrum of Organic Compound 1.

FIG. 18 illustrates the calculated Huang-Rhys factor of Organic Compound 1. FIG. 19 illustrates the calculated emission spectrum of Organic Compound 1. FIG. 18 shows that the calculated emission spectrum thereof has a first vibrational peak and a second vibrational peak and the intensity ratio of the second vibrational peak to the first vibrational peak is 0.7 or less.

Example 2

In this example, Organic Compound 2 having the following formula was designed and calculated for spectrum:

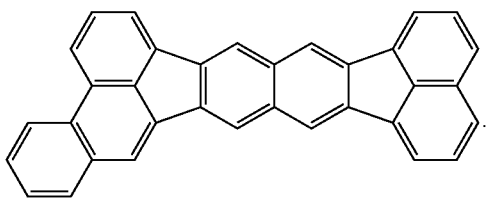
(2)

The PF of Organic Compound 2 was calculated in the same manner as that described in Example 1.

Figure 20:
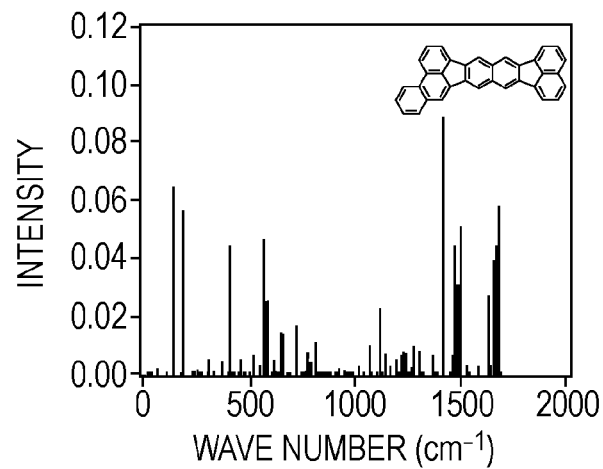
FIG. 20 is a graph illustrating the calculated Huang-Rhys factor of Organic Compound 2.
Figure 21:
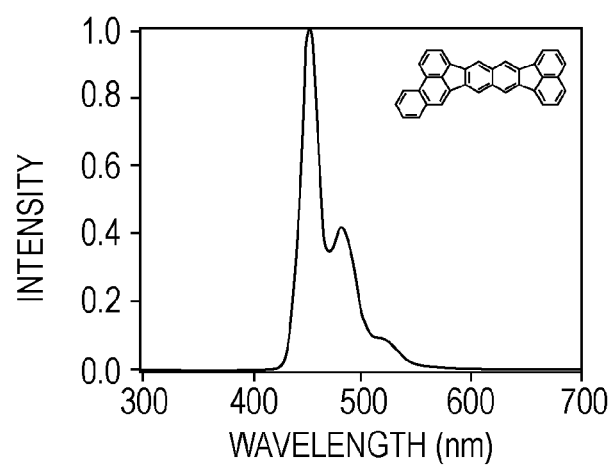
FIG. 21 is a graph illustrating the calculated emission spectrum of Organic Compound 2.

FIG. 20 illustrates the calculated Huang-Rhys factor of Organic Compound 2. FIG. 21 illustrates the calculated emission spectrum of Organic Compound 2.

Comparative Example 1

In this comparative example, Organic Compound 3 having the following formula was designed and calculated for spectrum:

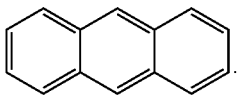
(3)

The PF of Organic Compound 3 was calculated in the same manner as that described in Example 1.

Figure 22:
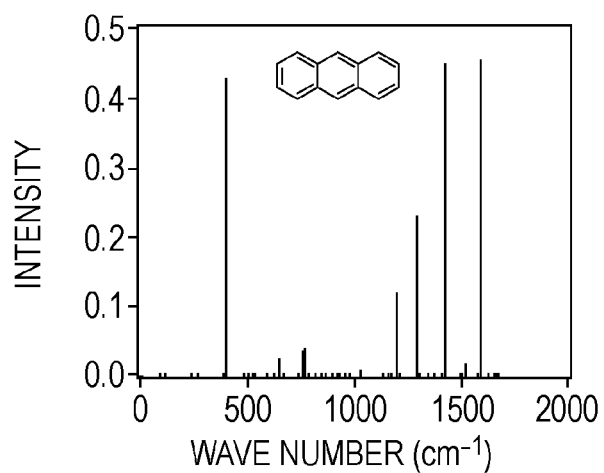
FIG. 22 is a graph illustrating the calculated Huang-Rhys factor of Organic Compound 3.
Figure 23:
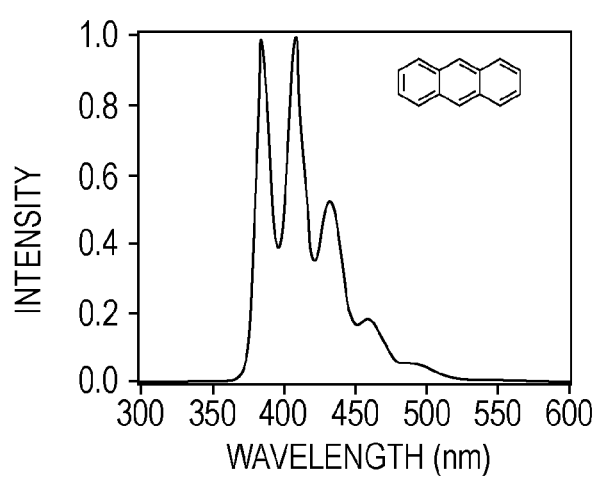
FIG. 23 is a graph illustrating the calculated emission spectrum of Organic Compound 3.

FIG. 22 illustrates the calculated Huang-Rhys factor of Organic Compound 3. FIG. 23 illustrates the calculated emission spectrum of Organic Compound 3.

Comparative Example 2

In this comparative example, Organic Compound 4 having the following formula was designed and calculated for spectrum:

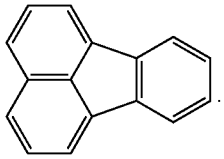
(4)

The PF of Organic Compound 4 was calculated in the same manner as that described in Example 1.

Figure 24:
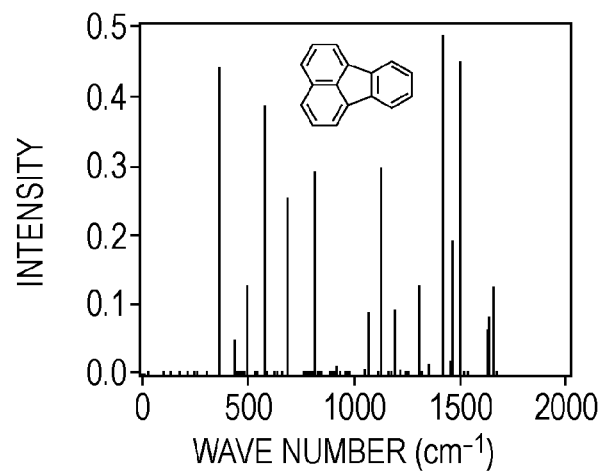
FIG. 24 is a graph illustrating the calculated Huang-Rhys factor of Organic Compound 4.
Figure 25:
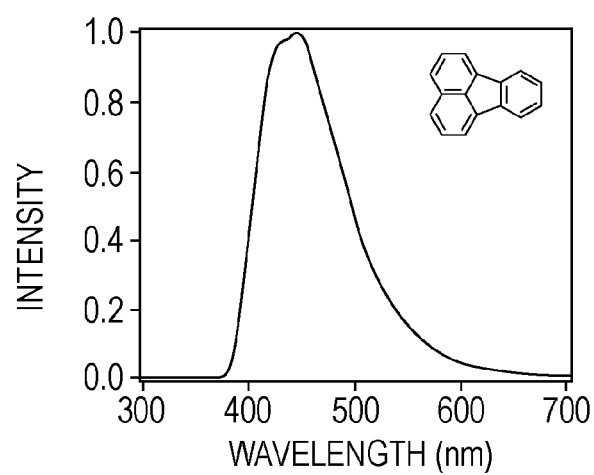
FIG. 25 is a graph illustrating the calculated emission spectrum of Organic Compound 4.

FIG. 24 illustrates the calculated Huang-Rhys factor of Organic Compound 4. FIG. 25 illustrates the calculated emission spectrum of Organic Compound 4.

Comparative Example 3

In this comparative example, Organic Compound 5 having the following formula was designed and calculated for spectrum:

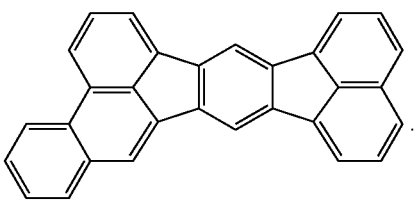
(5)

The PF of Organic Compound 5 was calculated in the same manner as that described in Example 1.

Figure 26:
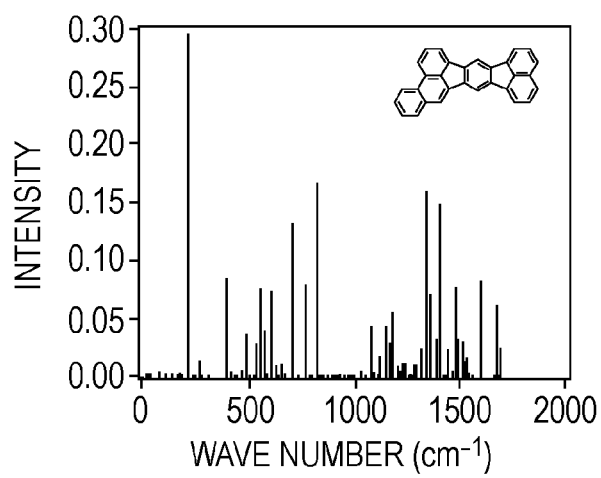
FIG. 26 is a graph illustrating the calculated Huang-Rhys factor of Organic Compound 5.
Figure 27:
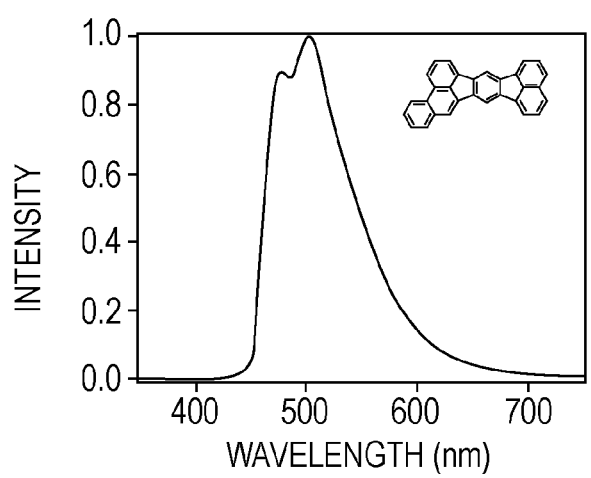
FIG. 27 is a graph illustrating the calculated emission spectrum of Organic Compound 5.

FIG. 26 illustrates the calculated Huang-Rhys factor of Organic Compound 5. FIG. 27 illustrates the calculated emission spectrum of Organic Compound 5.

Comparative Example 4

In this comparative example, Organic Compound 6 having the following formula was designed and calculated for spectrum:

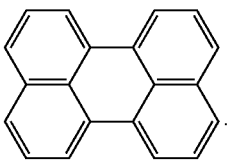
(6)

The PF of Organic Compound 6 was calculated in the same manner as that described in Example 1. As a result, the PF thereof was determined to be 0.0521.

Figure 28:
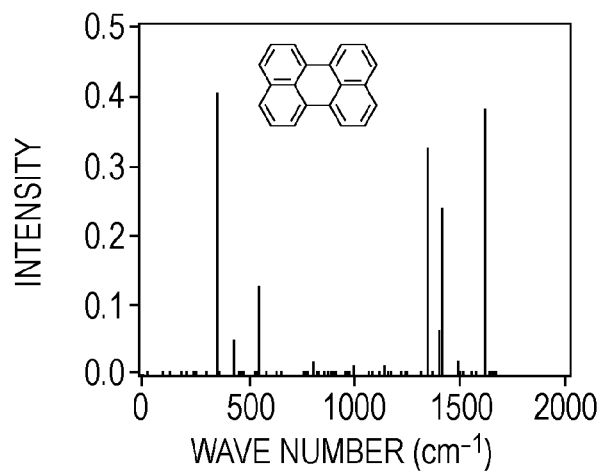
FIG. 28 is a graph illustrating the calculated Huang-Rhys factor of Organic Compound 6.
Figure 29:
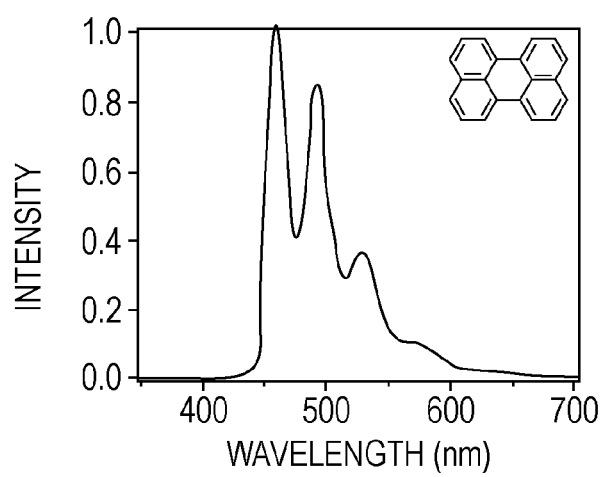
FIG. 29 is a graph illustrating the calculated emission spectrum of Organic Compound 6.

FIG. 28 illustrates the calculated Huang-Rhys factor of Organic Compound 6. FIG. 29 illustrates the calculated emission spectrum of Organic Compound 6.

Table 3 summarizes the PFs of the organic compounds of Examples 1 and 2 and Comparative Examples 1 to 4.

TABLE 3

| | Compounds | PF |
|---|---|---|
| Example 1 | | 0.0173 |

TABLE 3-continued

| | Compounds | PF |
|---|---|---|
| Example 2 | 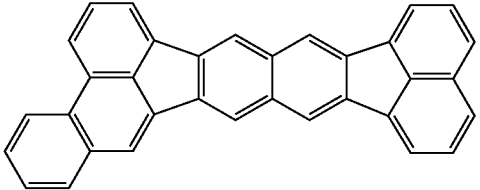 [SMILES: c1ccc2c(c1)cc1c3cc4cc5c(cc4cc3c3cccc2c31)c1cccc2cccc5c21] | 0.0129 |
| Comparative Example 1 | 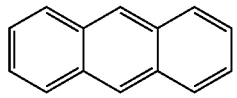 | 0.0918 |
| Comparative Example 2 | 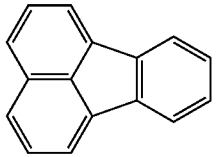 [SMILES: c1ccc2c(c1)-c1cccc3cccc-2c13] | 0.0980 |
| Comparative Example 3 | 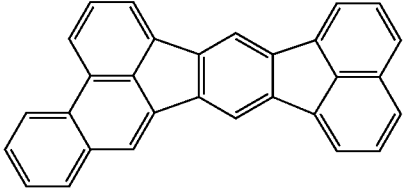 [SMILES: c1ccc2c(c1)cc1c3cc4c(cc3c3cccc2c31)c1cccc2cccc4c21] | 0.0282 |
| Comparative Example 4 | 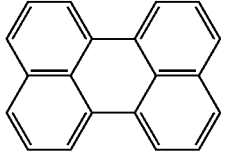 [SMILES: c1cc2cccc3c4cccc5cccc(c(c1)c23)c54] | 0.0521 |

As is clear from Table 3, the calculated PFs of the organic compounds of Examples 1 and 2 are not more than 0.02 and those of Comparative Examples 1 to 4 are greater than 0.02. The organic compounds of Examples 1 and 2 each have an emission spectrum having a first vibrational peak and a second vibrational peak and the intensity ratio of the second vibrational peak to the first vibrational peak is 0.7 or less.

On the basis of these results, the above organic compounds were actually synthesized or commercially obtained.

The organic compounds were measured for emission spectrum in such a manner that a $1 \times 10^{-5}$ mol/L solution of each organic compound in toluene was prepared and then analyzed with a Hitachi F-4500 spectrophotometer at an excitation wavelength of 350 nm. The syntheses of some of the organic compounds are described below.

Synthesis 1

The following compounds were synthesized with reference to Scheme 1 shown in *Chem. Commun.*, 2005, 21722174, p. 2172:

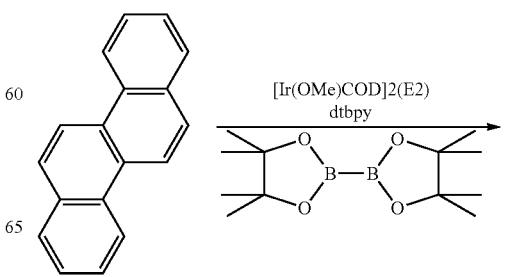

-continued

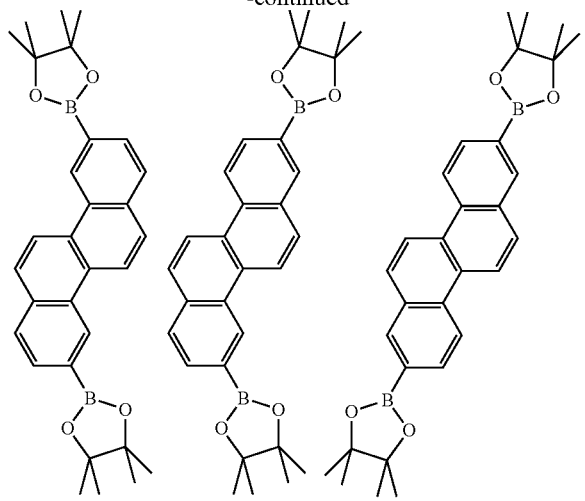

Organic Compound 1, described in Example 1, was synthesized from the above compounds under substantially the same conditions as those listed in FIG. 2 shown in *J. Org. Chem.*, 2003, 68, 883-887, p. 884 as follows:

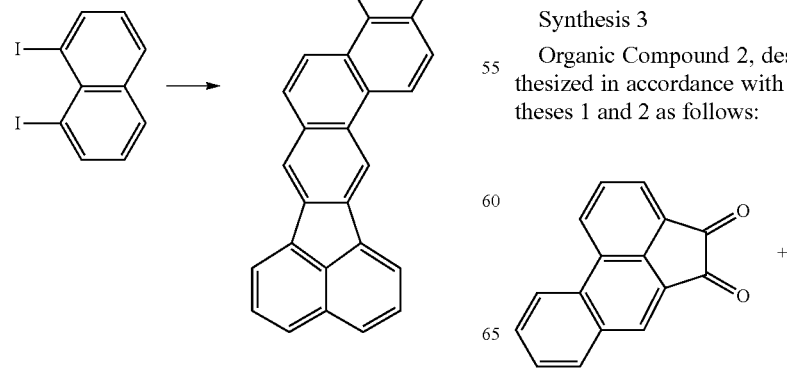

Synthesis 2

Organic Compound 5, described in Comparative Example 3, was synthesized with reference to Scheme 1 shown in J. Am. Chem. Soc., 2004, 126, 15974-15975 and *J. Org. Chem.*, 1964, 29 (10), 3129 as follows:

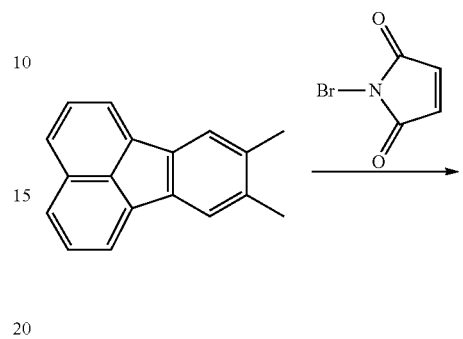

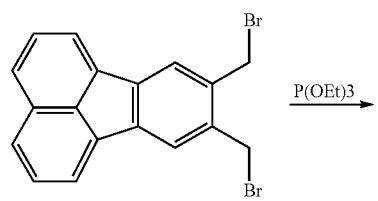

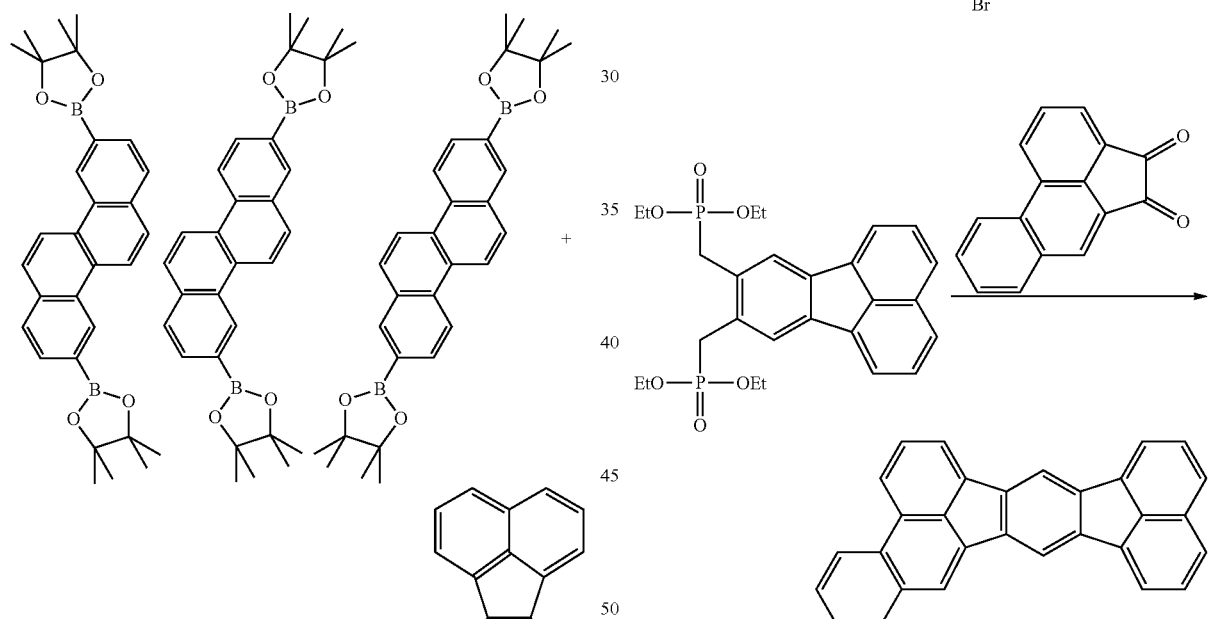

Synthesis 3

Organic Compound 2, described in Example 2, was synthesized in accordance with the reactions described in Syntheses 1 and 2 as follows:

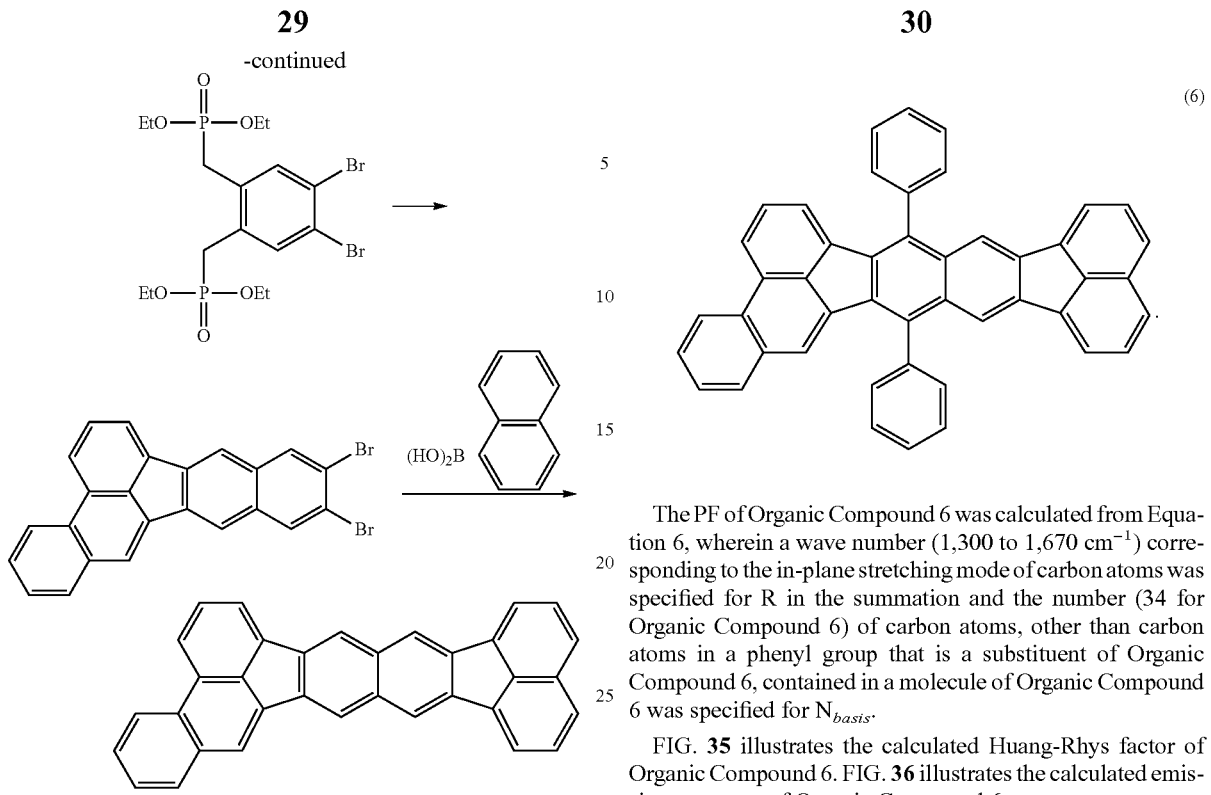

Figure 30:
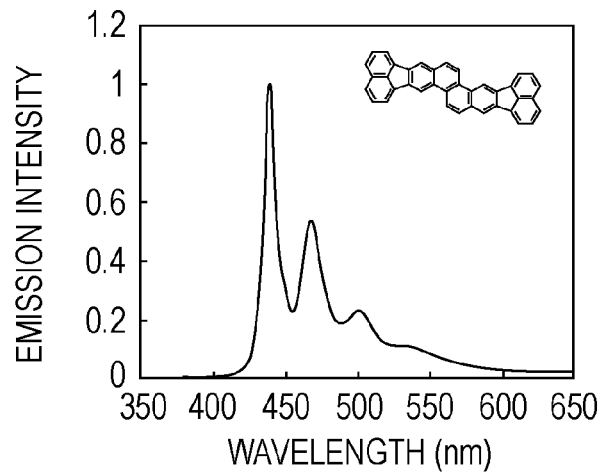
FIG. 30 is a graph illustrating the structure of the organic compound described in Example 1 and the emission spectrum of a toluene solution of the organic compound described therein.
Figure 31:
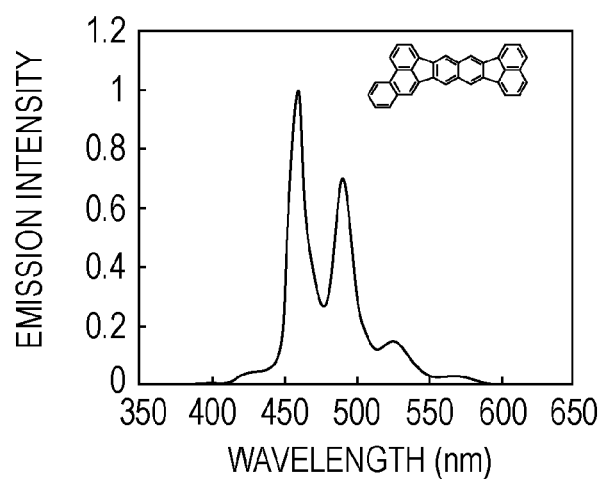
FIG. 31 is a graph illustrating the structure of the organic compound described in Example 2 and the emission spectrum of a toluene solution of the organic compound described therein.
Figure 32:
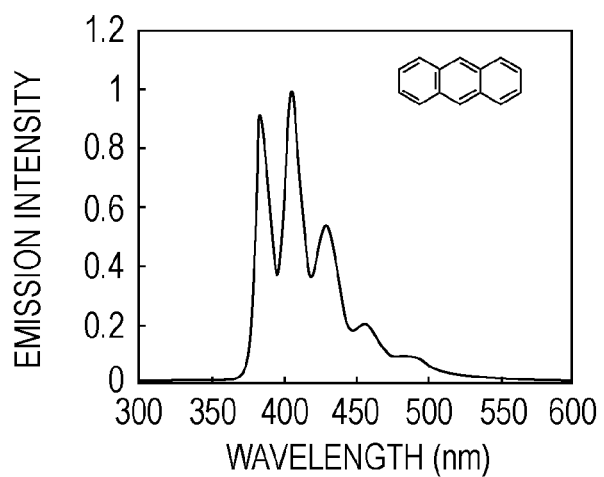
FIG. 32 is a graph illustrating the structure of the organic compound described in Comparative Example 1 and the emission spectrum of a toluene solution of the organic compound described therein.
Figure 33:
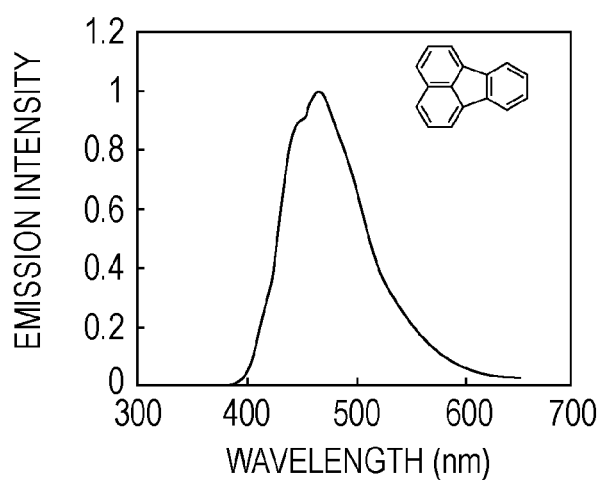
FIG. 33 is a graph illustrating the structure of the organic compound described in Comparative Example 2 and the emission spectrum of a toluene solution of the organic compound described therein.
Figure 34:
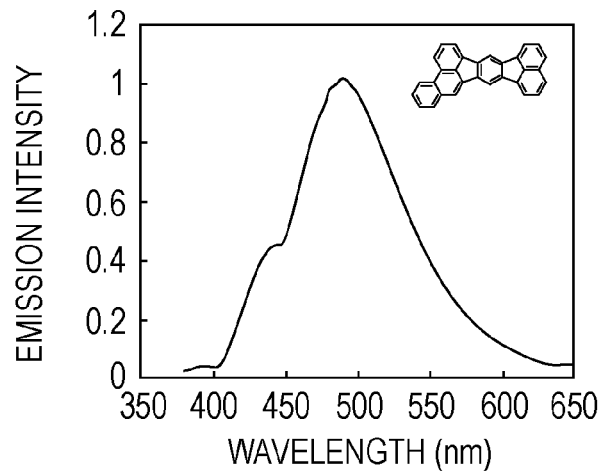
FIG. 34 is a graph illustrating the structure of the organic compound described in Comparative Example 3 and the emission spectrum of a toluene solution of the organic compound described therein.

Results obtained from Examples 1 and 2 and Comparative Examples 1 to 3 are shown in FIGS. 30 to 40. FIG. 30 is a graph illustrating the structure of the organic compound described in Example 1 and the emission spectrum of a toluene solution of the organic compound described therein. FIG. 31 is a graph illustrating the structure of the organic compound described in Example 2 and the emission spectrum of a toluene solution of the organic compound described therein. FIG. 32 is a graph illustrating the structure of the organic compound described in, Comparative Example 1 and the emission spectrum of a toluene solution of the organic compound described therein. FIG. 33 is a graph illustrating the structure of the organic compound described in Comparative Example 2 and the emission spectrum of a toluene solution of the organic compound described therein. FIG. 34 is a graph illustrating the structure of the organic compound described in Comparative Example 3 and the emission spectrum of a toluene solution of the organic compound described therein.

The calculated emission spectrum and measured emission spectrum of each of the organic compounds described in Examples 1 and 2 and Comparative Examples 1 to 3 have a similar waveform. This shows that quantum chemical calculation based on a Huang-Rhys factor is effective in predicting the waveform of the emission spectrum of an organic compound.

The measured emission spectra of the organic compounds having a PF of not more than 0.02 each have a first vibrational peak due to 0-0 vibration and a second vibrational peak and the intensity ratio of the second vibrational peak to the first vibrational peak is 0.7 or less. The first vibrational peak has a full width at half maximum of not more than 30 nm. This shows that a molecule (organic compound) most suitable for an organic light-emitting device can be designed.

Example 3

In this example, Organic Compound 6 having the following formula was designed and calculated for spectrum:

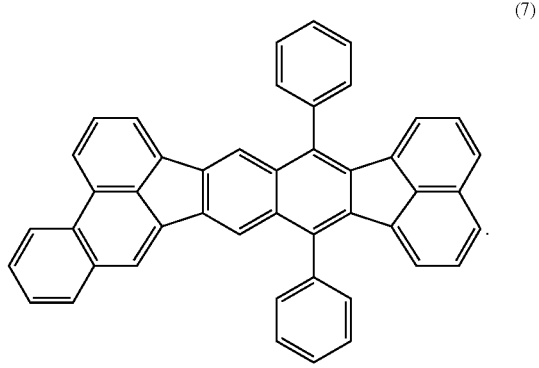 [SMILES: c1ccc(-c2c3cc4c(cc3c(-c3ccccc3)c3c5cccc6cccc(c23)c65)c2cc3ccccc3c3cccc4c32)cc1]

(6)

The PF of Organic Compound 6 was calculated from Equation 6, wherein a wave number (1,300 to 1,670 cm$^{-1}$) corresponding to the in-plane stretching mode of carbon atoms was specified for R in the summation and the number (34 for Organic Compound 6) of carbon atoms, other than carbon atoms in a phenyl group that is a substituent of Organic Compound 6, contained in a molecule of Organic Compound 6 was specified for $N_{basis}$.

Figure 35:
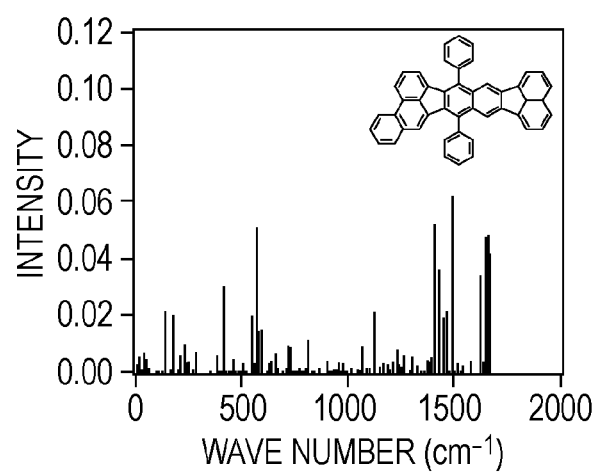
FIG. 35 is a graph illustrating the calculated Huang-Rhys factor of Organic Compound 6.
Figures 36, 37:
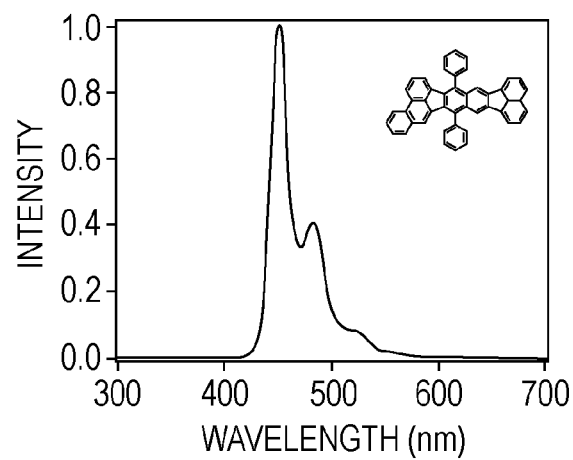
FIG. 36 is a graph illustrating the calculated emission spectrum of Organic Compound 6.
FIG. 37 is a graph illustrating the calculated Huang-Rhys factor of Organic Compound 7.

FIG. 35 illustrates the calculated Huang-Rhys factor of Organic Compound 6. FIG. 36 illustrates the calculated emission spectrum of Organic Compound 6.

Example 4

In this example, Organic Compound 7 having the following formula was designed and calculated for spectrum:

(7)

The PF of Organic Compound 7 was calculated in the same manner as that described in Example 3.

Figure 38:
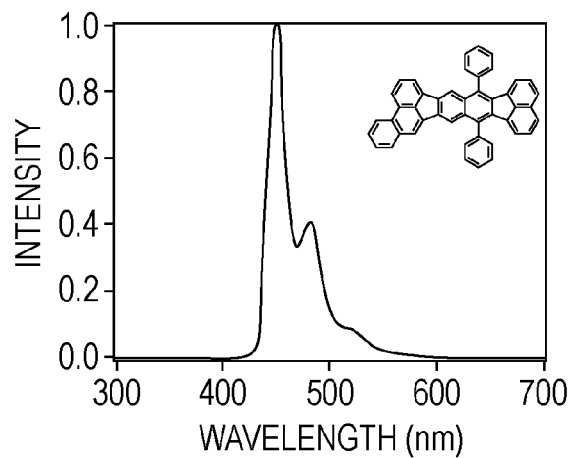
FIG. 38 is a graph illustrating the calculated emission spectrum of Organic Compound 7.

FIG. 37 illustrates the calculated Huang-Rhys factor of Organic Compound 7. FIG. 38 illustrates the calculated emission spectrum of Organic Compound 7.

Example 5

In this example, Organic Compound 8 having the following formula was designed and calculated for spectrum:

(8)

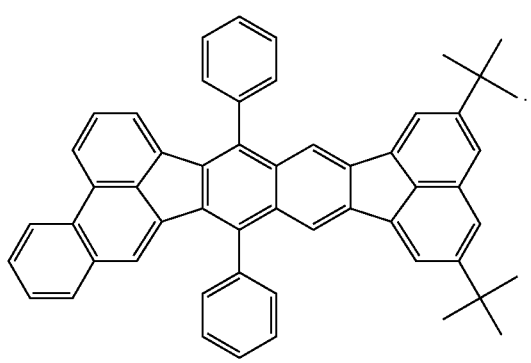

The PF of Organic Compound 8 was calculated in the same manner as that described in Example 3.

Figure 39:
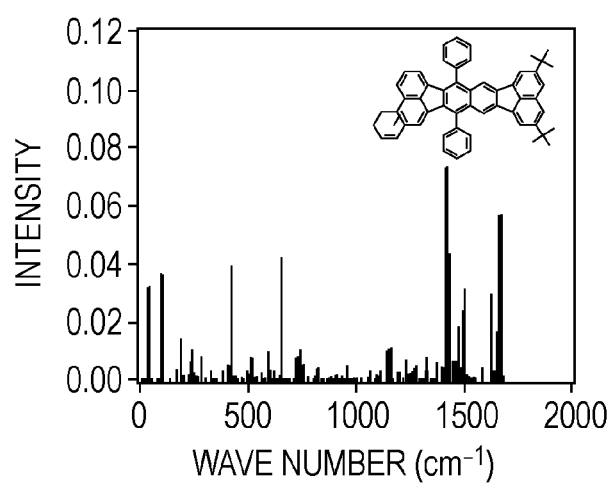
FIG. 39 is a graph illustrating the calculated Huang-Rhys factor of Organic Compound 8.
Figure 40:
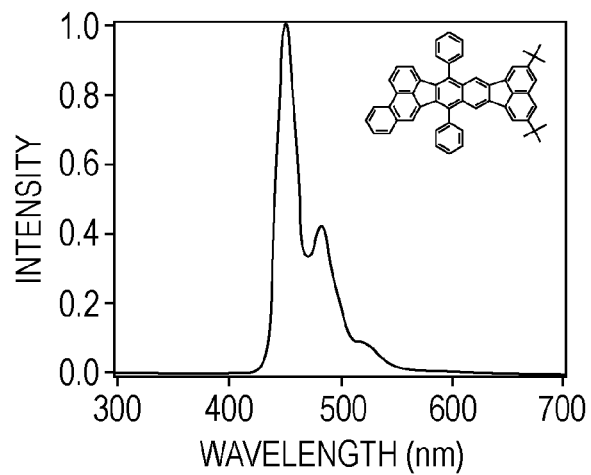
FIG. 40 is a graph illustrating the calculated emission spectrum of Organic Compound 8.

FIG. 39 illustrates the calculated Huang-Rhys factor of Organic Compound 8. FIG. 40 illustrates the calculated emission spectrum of Organic Compound 8.

Example 6

In this example, Organic Compound 9 having the following formula was designed and calculated for spectrum:

(9)

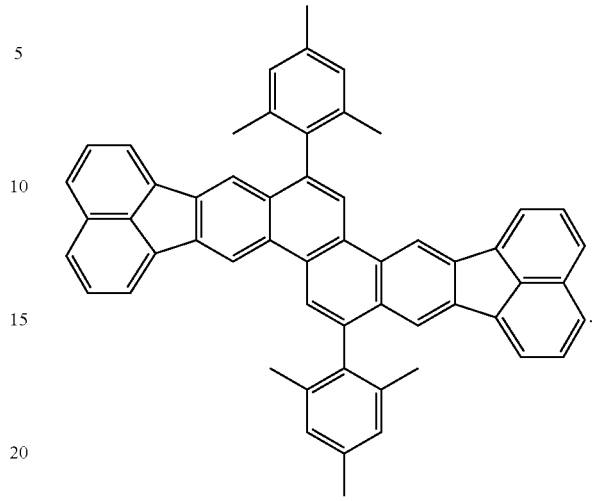

The PF of Organic Compound 9 was calculated in the same manner as that described in Example 3.

Figure 41:
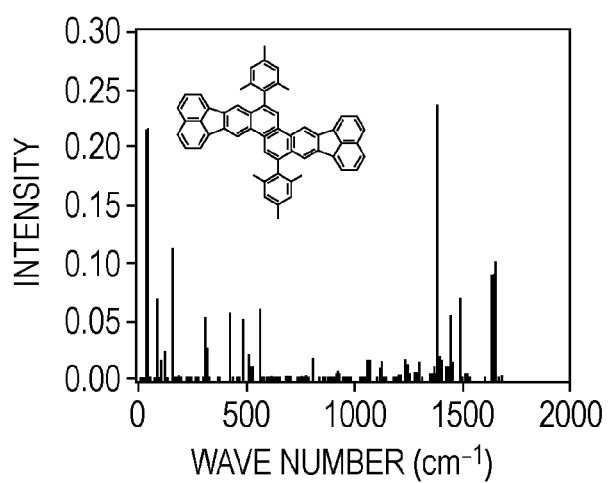
FIG. 41 is a graph illustrating the calculated Huang-Rhys factor of Organic Compound 9.
Figure 42:
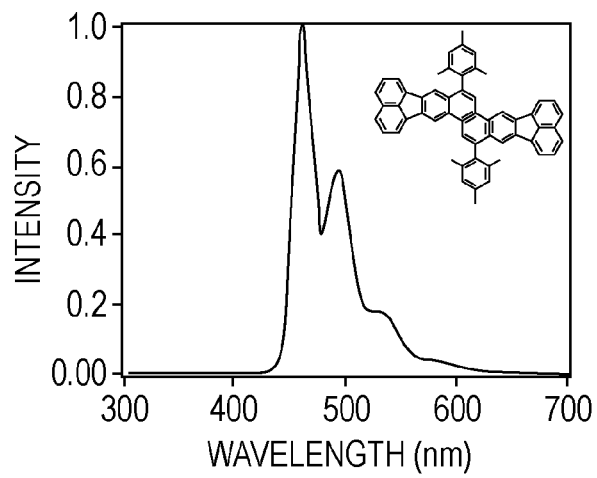
FIG. 42 is a graph illustrating the calculated emission spectrum of Organic Compound 9.

FIG. 41 illustrates the calculated Huang-Rhys factor of Organic Compound 9. FIG. 42 illustrates the calculated emission spectrum of Organic Compound 9.

Table 4 summarizes the PFs of the organic compounds of Examples 1 to 6.

TABLE 4

| | Compounds | PF |
|---|---|---|
| Example 1 | | 0.0173 |
| Example 2 | | 0.0129 |
| Example 3 | | 0.0130 |

TABLE 4-continued

| | Compounds | PF |
|---|---|---|
| Example 4 | (structure) | 0.0129 |
| Example 5 | (structure) | 0.0133 |
| Example 6 | (structure) | 0.0177 |

As is clear from Table 4, the organic compounds of Examples 1 to 4 contain no substituent and have a PF of not more than 0.02 and the organic compounds of Examples 5 and 6 contain substituents and have a PF of not more than 0.02. That is, the PFs of the organic compounds of Examples 1 to 4 are not significantly different from those of Examples 5 and 6.

The organic compounds of Examples 3 and 6 were measured for emission spectrum in such a manner that a $1\times10^{-5}$ mol/L solution of each organic compound in toluene was prepared and then analyzed with a Hitachi F-4500 spectrophotometer at an excitation Wavelength of 350 nm.

Figure 43:
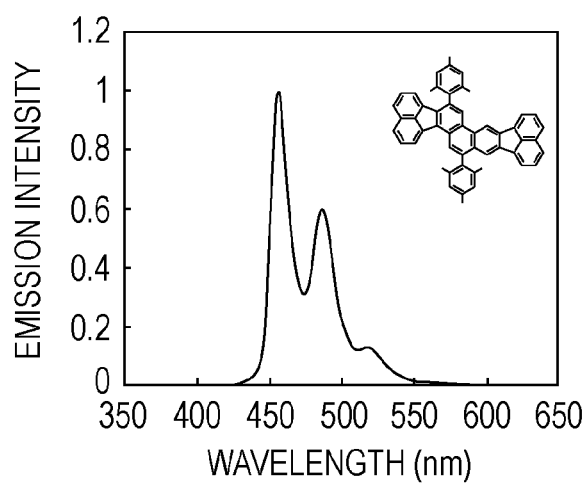
FIG. 43 is a graph illustrating the emission spectrum of the organic compound of Example 6.
Figure 44:
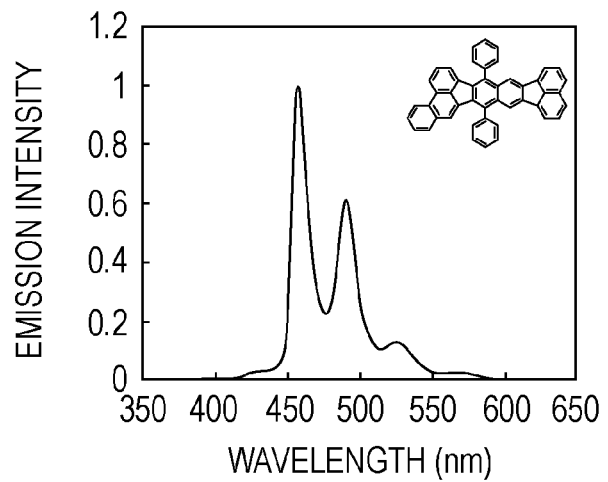
FIG. 44 is a graph illustrating the emission spectrum of the organic compound of Example 3.

FIG. 43 illustrates the emission spectrum of the organic compound of Example 6. FIG. 44 illustrates the emission spectrum of the organic compound of Example 3. The emission spectra of the organic compounds of Examples 3 and 6 are not significantly different from each other, although the organic compound of Example 6 contains substituents. The organic compounds of Examples 3 and 6 have a PF of not more than 0.02. The emission spectra of the organic compounds thereof have a first vibrational peak due to 0-0 vibration and a second vibrational peak and the intensity ratio of the second vibrational peak to the first vibrational peak is 0.7 or less. The first vibrational peak has a full width at half maximum of not more than 30 nm.

Comparative Examples 4 to 7

The PFs of organic compounds below were determined. Table 5 summarizes the results.

TABLE 5

| | Compounds | PF |
|---|---|---|
| Comparative Example 5 | | 0.0240 |
| Comparative Example 6 | | 0.0317 |
| Comparative Example 7 | | 0.0240 |
| Comparative Example 8 | | 0.0410 |

As is clear from Table 5, the organic compounds of Comparative Examples 4 to 7 have a PF of greater than 0.02.

Example 7 and Comparative Examples 8 and 9

In each of Example 7 and Comparative Examples 8 and 9, the following device was prepared: an organic light-emitting device including an anode, a hole injection layer, a hole transport layer, a light-emitting layer, an electron transport layer, an electron injection layer, and a cathode as shown in the fifth example of the multilayer-type organic light-emitting device described in the second embodiment.

The organic light-emitting device was prepared by a procedure below so as to have an optical resonator structure.

An aluminum alloy (Al—Nd) was deposited on a glass substrate serving as a support member by sputtering, whereby a reflective portion of the anode was formed so as to have a thickness of 100 nm. A transparent portion of the anode was formed so as to have a thickness of 80 nm by sputtering using ITO. An element isolation layer, made of an acrylic resin, having a thickness of 1.5 μm was provided around the anode and an opening with a radius of 3 mm was formed therein. The glass substrate was ultrasonically cleaned with acetone and isopropyl alcohol (IPA) in that order, cleaned with boiling IPA, and then dried. Furthermore, surfaces of the glass substrate were subjected to UV/ozone cleaning.

In a vacuum chamber with a pressure of $10^{-5}$ Pa, organic layers below were continuously formed on the anode by resistive heating vacuum deposition and the cathode was then formed on the top of the organic layers by sputtering using indium zinc oxide (IZO). The anode had a thickness of 30 nm and was transparent. The glass substrate carrying these components was sealed in a nitrogen atmosphere.

The organic light-emitting device was obtained by the above procedure.

A guest material used in Example 7 was Organic Compound G-1, designed by molecular orbital calculation, having the following formula:

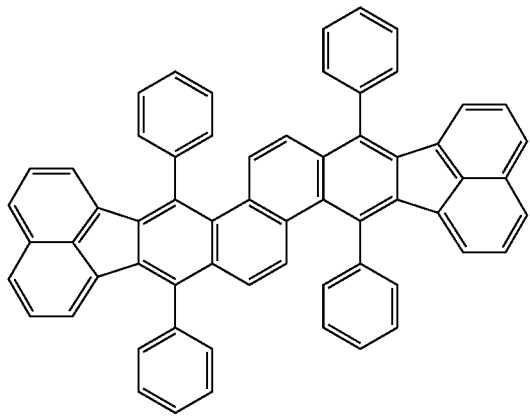

G1

A guest material used in Comparative Example 8 was Organic Compound G-2 having a PF of 0.41, no vibrational structure, and the following formula:

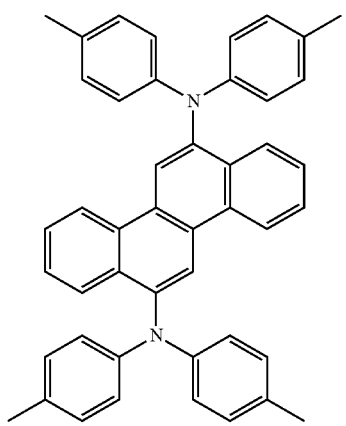

G2

A guest material used in Comparative Example 9 was Organic Compound G-3 having a vibrational structure, an emission spectrum in which the intensity ratio of a second vibrational peak to a first vibrational peak was about 0.9, and the following formula:

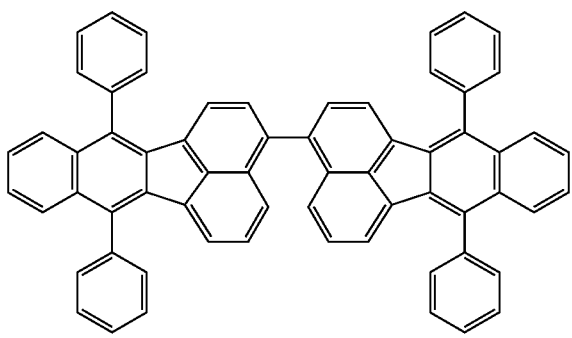 [SMILES: c1ccc(-c2c3c(c(-c4ccccc4)c4ccccc24)-c2ccc(-c4ccc5c6c(cccc46)-c4c-5c(-c5ccccc5)c5ccccc5c4-c4ccccc4)c4cccc-3c24)cc1]

G3

The hole injection layer had a thickness of 95 nm and was made of Organic Compound H-1 having the following formula:

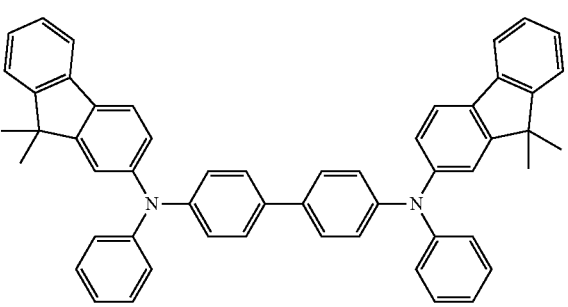

H-1

The hole transport layer had a thickness of 10 nm and was made of Organic Compound H-2 having the following formula:

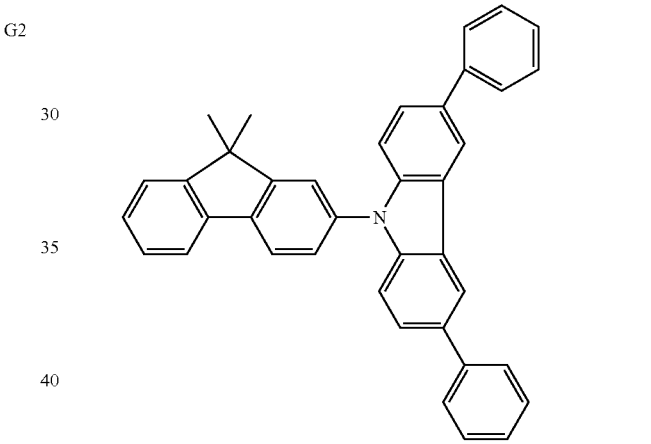

H-2

The light-emitting layer had a thickness of 35 nm and was made of Organic Compound H-3 having the following formula:

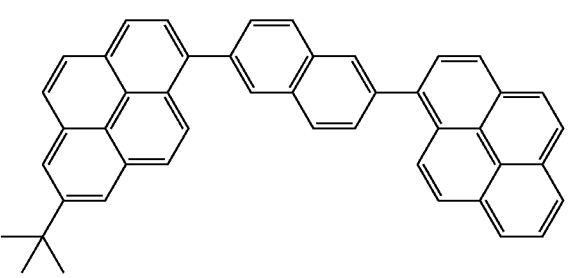

H-3

A guest material used was an exemplary compound and had a weight content of 2%.

The electron transport layer had a thickness of 10 nm and was made of Organic Compound H-4 having the following formula:

H-4

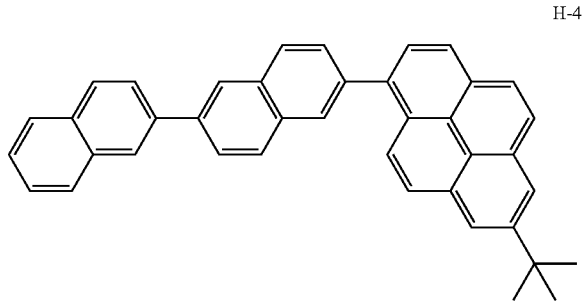

The electron injection layer had a thickness of 70 nm and contained 80% by weight of Organic Compound H-5 having the following formula and 20% by weight of Li:

H-5

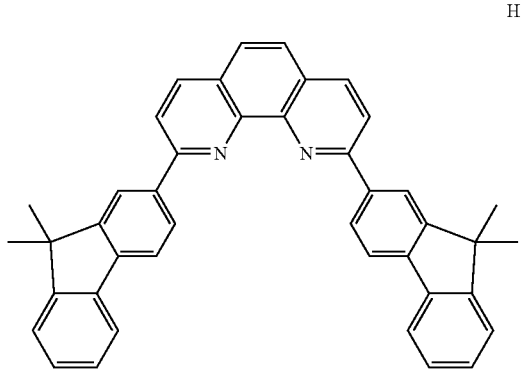

Organic Compounds G1 to G3 were measured for emission spectrum (photoluminescence spectrum) in such a manner that a $1\times10^{-5}$ mol/L solution of each organic compound in toluene was analyzed with a Hitachi F-4500 spectrophotometer at an excitation wavelength of 350 nm.

Figure 45:
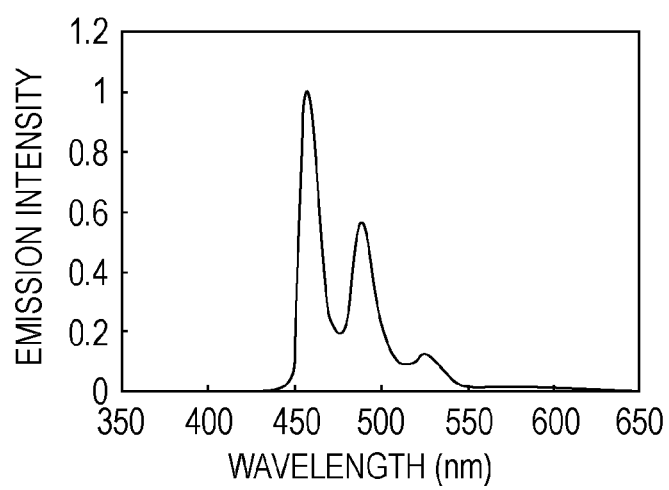
FIG. 45 is a graph illustrating the photoluminescence spectrum of Organic Compound G1.
Figure 46:
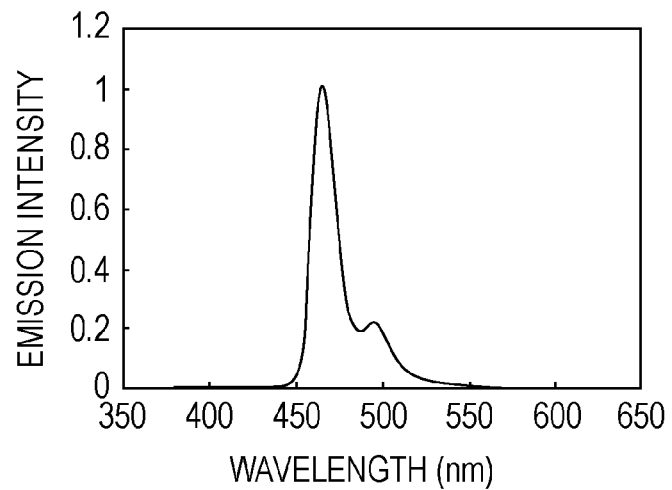
FIG. 46 is a graph illustrating the emission spectrum of the organic light-emitting device of Example 7.

FIG. 45 illustrates the photoluminescence spectrum of Organic Compound G1. FIG. 46 illustrates the emission spectrum of the organic light-emitting device of Example 7.

Figure 47:
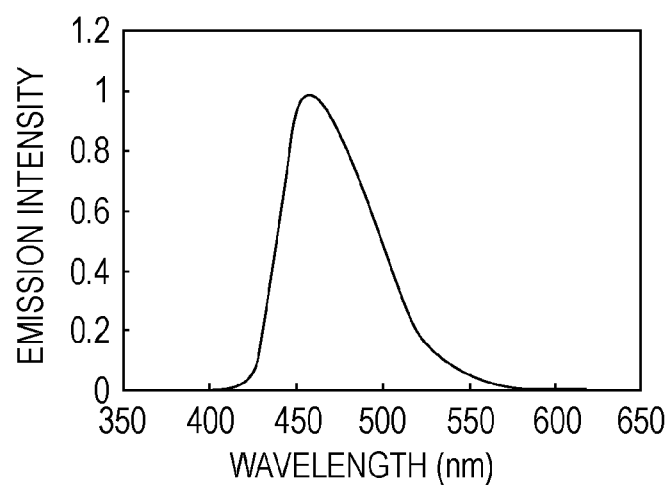
FIG. 47 is a graph illustrating the photoluminescence spectrum of Organic Compound G2.
Figure 48:
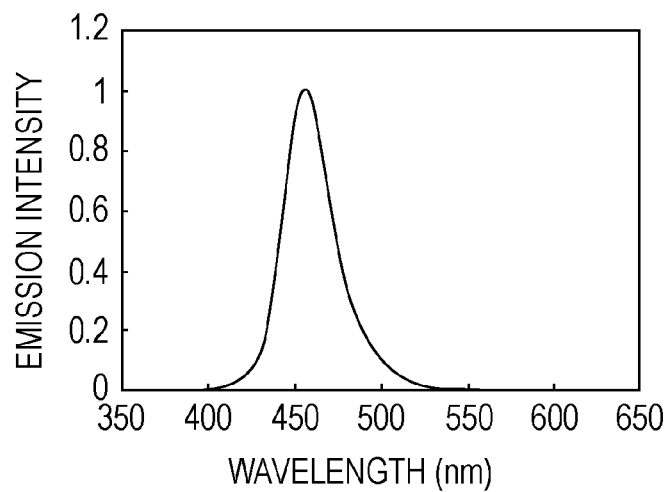
FIG. 48 is a graph illustrating the emission spectrum of the organic light-emitting device of Comparative Example 8.

FIG. 47 illustrates the photoluminescence spectrum of Organic Compound G2. FIG. 48 illustrates the emission spectrum of the organic light-emitting device of Comparative Example 8

Figure 49:
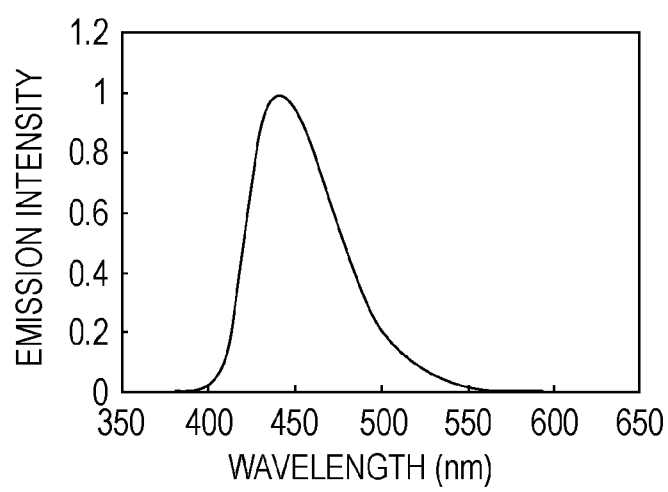
FIG. 49 is a graph illustrating the photoluminescence spectrum of Organic Compound G3.
Figure 50:
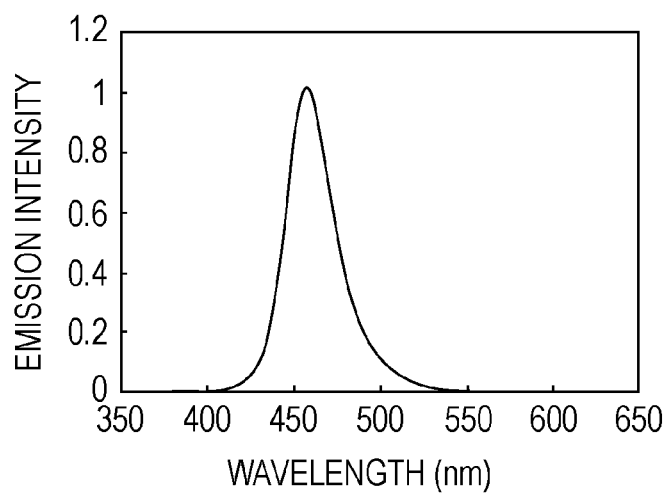
FIG. 50 is a graph illustrating the emission spectrum of the organic light-emitting device of Comparative Example 9.

FIG. 49 illustrates the photoluminescence spectrum of Organic Compound G3. FIG. 50 illustrates the emission spectrum of the organic light-emitting device of Comparative Example 9.

Comparative Example 10

Figure 51:
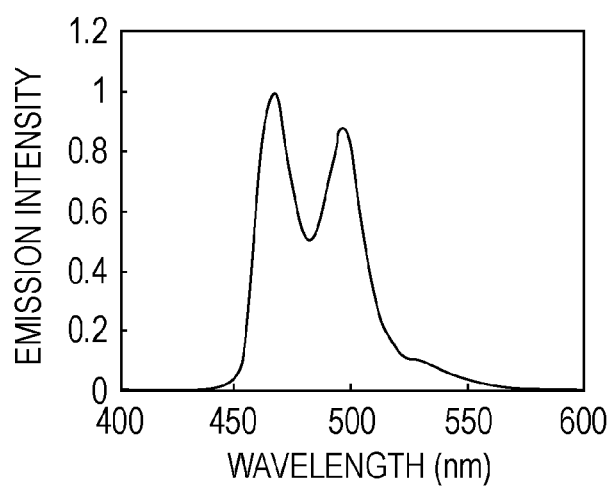
FIG. 51 illustrates the emission spectrum of the organic light-emitting device of Comparative Example 10.

An organic light-emitting device identical in configuration to that of Example 7 was prepared except that the organic light-emitting device included a hole injection layer with a thickness of 115 nm. FIG. 51 illustrates the emission spectrum of the organic light-emitting device.

The photoluminescence (PL) of the materials used in Example 7 and Comparative Examples 8 and 9 was compared to the electroluminescence (EL) of the organic light-emitting devices of Example 7 and Comparative Examples 8 and 9 as summarized in Table 6, the organic light-emitting devices using optical interference.

TABLE 6

| Compounds | | Example 7 | Comparative Example 8 | Comparative Example 9 |
|---|---|---|---|---|
| PF | | 0.018 | 0.041 | 0.033 |
| Photoluminescent area | X | 100 | 100 | 100 |
| Photoluminescent chromaticity | Y | 0.13 | 0.14 | 0.14 |
| | | 0.15 | 0.13 | 0.15 |
| Photoluminescent area | | 80.7 | 61.7 | 69.8 |
| Electroluminescent chromaticity | X | 0.12 | 0.14 | 0.12 |
| | Y | 0.10 | 0.08 | 0.11 |
| Percentage of area unused for electroluminescence (%) | | 19.3 | 38.3 | 30.2 |

As is clear from the results shown in Table 6, the organic light-emitting devices which include the optical resonator structures using optical interference have increased color purity. In the case of using a material with an emission spectrum with a narrow full width at half maximum in a light-emitting device using optical interference, the loss of luminescence of the material can be reduced.

As is clear from FIG. 51, the shift of the optical interference path from an optical resonator structure causes the waveform of light to be significantly shifted and also causes chromaticity far inferior to necessary chromaticity. The organic compound designed herein can exhibit advantages by the use of an optical resonator structure.

Results and Considerations

An organic compound with a PF of 0.02 as determined from quantum chemical calculation has a vibrational structure and an emission spectrum having a first vibrational peak with a full width at half maximum of not more than 30 nm and a second vibrational peak. The intensity ratio of the second vibrational peak to the first vibrational peak is 0.7 or less.

An organic light-emitting device according to the present invention contains such an organic compound and has an optical resonator structure with an optical thickness nd given by the following equation:

$$nd=(2N-1)\lambda/4$$

wherein n is the refractive index, d is the distance from the luminescent center, λ is the peak wavelength of emitted light, and N is a positive integer. Therefore, the organic light-emitting device has lower emission loss and higher color purity as compared to organic light-emitting devices containing organic compounds with a wide full width at half maximum.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

What is claimed is:

1. An organic light-emitting device comprising:
   a pair of electrodes; and
   a light-emitting layer being interposed between the pair of electrodes and having an organic compound which emits light,
   wherein an emission spectrum of the organic compound has a first peak and a second peak, the first peak being the highest intensity among the emission spectrum, and the second peak having a wavelength longer than a wavelength of the first peak,
   wherein the first peak has a full width at half maximum of 30 nm or less and the wavelength of the first peak is from 430 nm to 480 nm,
   wherein an intensity ratio of the second peak to the first peak is 0.7 or less, and
   wherein the emission spectrum is a photoluminescence spectrum which is obtained by analysis of a toluene solution having the organic compound.

2. The organic light-emitting device according to claim 1, wherein
   the light-emitting layer has a guest material and a host material,
   the guest material is the organic compound,
   the host material is another organic compound, and a LUMO level of the guest material is lower than a LUMO level of the host material.

3. The organic light-emitting device according to claim 1, wherein
   the light-emitting layer has a guest material and a host material,
   the guest material is the organic compound,
   the host material is another organic compound,
   a LUMO level of the guest material is lower than a LUMO level of the host material, and
   a HOMO level of the guest material is higher than a HOMO level of the host material.

4. The organic light-emitting compound according to claim 1, wherein
   the light-emitting layer has a guest material and a host material,
   the guest material is the organic compound,
   the host material is another organic compound, and
   a HOMO level of the guest material is higher than a HOMO level of the host material.

5. The organic light-emitting device according to claim 2, wherein
   the guest material is an aromatic compound containing a five-membered ring.

6. The organic light-emitting device according to claim 3, wherein
   the guest material is an aromatic compound containing a five-membered ring.

7. The organic light-emitting device according to claim 1, wherein
   the light-emitting layer has a guest material and a host material,
   the guest material is the organic compound, and
   the host material is another organic compound which is any one of a condensed ring compound, an organoaluminum complex, the organozinc complex, a triphenylamine derivative and a polymeric derivative.

8. The organic light-emitting device according to claim 1, wherein
   the organic light-emitting device has an optical resonator structure containing a light reflective portion and a light extraction portion.

9. The organic light-emitting device according to claim 1, further comprising:
   a substrate,
   wherein the light emitted by the organic compound comes out from a substrate side.

10. The organic light-emitting device according to claim 1, further comprising:
    a substrate,
    wherein the light emitted by the organic compound comes out from an opposite side to a substrate side.

11. A display apparatus comprising:
    a plurality of the organic-emitting device according to claim 1;
    a scanning signal line; and
    an information signal line,
    wherein the scanning signal line and the information signal line are connected to the organic-emitting device.

12. A display apparatus comprising:
    a plurality of the organic-emitting device according to claim 2;
    a scanning signal line; and
    an information signal line,
    wherein the scanning signal line and the information signal line are connected to the organic-emitting device.

13. A display apparatus comprising:
    a plurality of the organic-emitting device according to claim 3;

a scanning signal line; and
an information signal line,
wherein the scanning signal line and the information signal line are connected to the organic-emitting device.

14. A display apparatus comprising:
a plurality of the organic-emitting device according to claim 4;
a scanning signal line; and
an information signal line,
wherein the scanning signal line and the information signal line are connected to the organic-emitting device.

15. A display apparatus comprising:
a plurality of the organic-emitting device according to claim 5;
a scanning signal line; and
an information signal line,
wherein the scanning signal line and the information signal line are connected to the organic-emitting device.

16. A display apparatus comprising:
a plurality of the organic-emitting device according to claim 6;
a scanning signal line; and
an information signal line,
wherein the scanning signal line and the information signal line are connected to the organic-emitting device.

17. A display apparatus comprising:
a plurality of the organic-emitting device according to claim 7;
a scanning signal line; and
an information signal line,
wherein the scanning signal line and the information signal line are connected to the organic-emitting device.

18. A display apparatus comprising:
a plurality of the organic-emitting device according to claim 8;
a scanning signal line; and
an information signal line,
wherein the scanning signal line and the information signal line are connected to the organic-emitting device.

19. A display apparatus comprising:
a plurality of the organic-emitting device according to claim 9;
a scanning signal line; and
an information signal line,
wherein the scanning signal line and the information signal line are connected to the organic-emitting device.

20. A display apparatus comprising:
a plurality of the organic-emitting device according to claim 10;
a scanning signal line; and
an information signal line,
wherein the scanning signal line and the information signal line are connected to the organic-emitting device.

21. An image pickup apparatus comprising:
a display unit comprising a display apparatus according to claim 11; and
an image pickup unit.

22. An image pickup apparatus comprising:
a display unit comprising a display apparatus according to claim 12; and
an image pickup unit.

23. An image pickup apparatus comprising:
a display unit comprising a display apparatus according to claim 13; and
an image pickup unit.

24. An image pickup apparatus comprising:
a display unit comprising a display apparatus according to claim 14; and
an image pickup unit.

25. An image pickup apparatus comprising:
a display unit comprising a display apparatus according to claim 15; and
an image pickup unit.

26. An image pickup apparatus comprising:
a display unit comprising a display apparatus according to claim 16; and
an image pickup unit.

27. An image pickup apparatus comprising:
a display unit comprising a display apparatus according to claim 17; and
an image pickup unit.

28. An image pickup apparatus comprising:
a display unit comprising a display apparatus according to claim 18; and
an image pickup unit.

29. An image pickup apparatus comprising:
a display unit comprising a display apparatus according to claim 19; and
an image pickup unit.

30. An image pickup apparatus comprising:
a display unit comprising a display apparatus according to claim 20; and
an image pickup unit.

31. An electrophotographic image-forming apparatus comprising:
a light source having a plurality of organic light-emitting device according to claim 1; and
a photoreceptor obtaining a latent image by the light source.

32. An lighting apparatus comprising:
an organic light-emitting device according to claim 1.

* * * * *